United States Patent
Chen et al.

(10) Patent No.: US 11,389,445 B2
(45) Date of Patent: Jul. 19, 2022

(54) PENTAFLUOROSULFANYL-SUBSTITUTED AMIDE DERIVATIVES, PREPARATION METHODS THEREOF AND MEDICAL USES THEREOF

(71) Applicant: Beijing Innocare Pharma Tech Co., Ltd., Beijing (CN)

(72) Inventors: Xiangyang Chen, Beijing (CN); Yucheng Pang, Beijing (CN)

(73) Assignee: Beijing Innocare Pharma Tech Co., Ltd., Beijing (CN)

( * ) Notice: Subject to any disclaimer, the term of this patent is extended or adjusted under 35 U.S.C. 154(b) by 0 days.

(21) Appl. No.: 16/965,546

(22) PCT Filed: Jan. 28, 2019

(86) PCT No.: PCT/CN2019/000019
§ 371 (c)(1),
(2) Date: Jul. 28, 2020

(87) PCT Pub. No.: WO2019/144781
PCT Pub. Date: Aug. 1, 2019

(65) Prior Publication Data
US 2021/0046069 A1    Feb. 18, 2021

(30) Foreign Application Priority Data
Jan. 29, 2018   (CN) .......................... 201810075173.8

(51) Int. Cl.
| | |
|---|---|
| *C07D 215/14* | (2006.01) |
| *A61K 31/496* | (2006.01) |
| *A61K 31/44* | (2006.01) |
| *A61K 31/47* | (2006.01) |
| *A61K 31/4709* | (2006.01) |
| *A61K 31/519* | (2006.01) |
| *A61K 45/06* | (2006.01) |
| *C07D 401/04* | (2006.01) |
| *C07D 487/04* | (2006.01) |

(52) U.S. Cl.
CPC ............ *A61K 31/496* (2013.01); *A61K 31/44* (2013.01); *A61K 31/47* (2013.01); *A61K 31/4709* (2013.01); *A61K 31/519* (2013.01); *A61K 45/06* (2013.01); *C07D 215/14* (2013.01); *C07D 401/04* (2013.01); *C07D 487/04* (2013.01)

(58) Field of Classification Search
None
See application file for complete search history.

(56) References Cited

FOREIGN PATENT DOCUMENTS

| CN | 103298808 A | 9/2013 |
|---|---|---|
| CN | 105481789 A | 4/2016 |
| CN | 106999450 A | 8/2017 |
| CN | 107205970 A | 9/2017 |
| CN | 107427499 A | 12/2017 |
| WO | WO-2006122150 A1 | 11/2006 |
| WO | WO-2011056652 A1 | 5/2011 |
| WO | WO-2013069765 A1 | 5/2013 |
| WO | WO-2014186035 A1 | 11/2014 |
| WO | WO-2015002918 A1 | 1/2015 |
| WO | WO-2016/073774 A2 | 5/2016 |
| WO | WO-2016073738 A2 | 5/2016 |
| WO | WO-2016073770 A1 | 5/2016 |
| WO | WO-2016/161960 A1 | 10/2016 |
| WO | WO-2016181348 A1 | 11/2016 |
| WO | WO-2017079669 A1 | 5/2017 |

OTHER PUBLICATIONS

Koblish et.al., "Hydroxyamidine Inhibitors of Indoleamine-2,3-dioxygenase Potently Suppress Systemic Tryptophan Catabolism and the Growth of IDO-Expressing Tumors," Mol. Cancer Ther., 9(2): 489-498 (2010).
Extended European Search Report for EP Application No. 19743196.8 dated Sep. 16, 2021.
Sowaileh et al., "Application of the Pentafluorosulfanyl Group as a Bioisosteric Replacement," ChemMedChem Communications, 12(18): 1481-1490 (2017).

*Primary Examiner* — Heidi Reese
(74) *Attorney, Agent, or Firm* — Foley Hoag LLP

(57) ABSTRACT

The present invention relates to a novel pentafluorosulfanyl-substituted amide compound that regulates or inhibits indoleamine 2,3-dioxygenase (IDO) activity, its preparation method and its application in medicine. Specifically, the present invention relates to a compound represented by general formula (I) and pharmaceutically acceptable salt thereof, a pharmaceutical composition containing the compound or pharmaceutically acceptable salt thereof, application of the compound or pharmaceutically acceptable salt thereof for treating and/or preventing related disorders mediated by IDO, especially tumors, and a method for preparing the compound or pharmaceutically acceptable salt thereof. The present invention also relates to the preparation of the compound or pharmaceutically acceptable salt thereof or a pharmaceutical composition containing the compound or pharmaceutically acceptable salt thereof for the treatment and/or prevention of IDO-mediated related disorders, especially for use in tumor treatment. The substituents in the general formula (I) are the same as described in the specification.

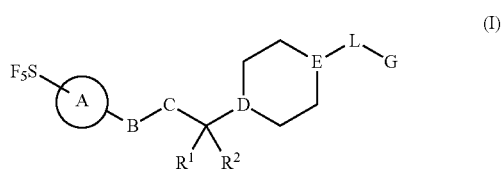

5 Claims, No Drawings

PENTAFLUOROSULFANYL-SUBSTITUTED AMIDE DERIVATIVES, PREPARATION METHODS THEREOF AND MEDICAL USES THEREOF

RELATED APPLICATIONS

This application is the U.S. National Phase of International Patent Application No. PCT/CN2019/000019, filed Jan. 28, 2019; which claims the benefit of priority to Chinese Patent Application No. CN 201810075173.8, filed Jan. 29, 2018.

FIELD OF THE INVENTION

The present invention relates to novel pentafluorosulfanyl-substituted amide derivatives or their pharmaceutically acceptable salts thereof, the pharmaceutical compositions containing the pentafluorosulfanyl-substituted amide derivatives or their pharmaceutically acceptable salts thereof, the methods for preparing the pentafluorosulfanyl-substituted amide derivatives or their pharmaceutically acceptable salts thereof, and the uses of the pentafluorosulfanyl-substituted amide derivatives or their pharmaceutically acceptable salts thereof, or the pharmaceutical compositions containing the pentafluorosulfanyl-substituted amide derivatives or their pharmaceutically acceptable salts thereof in the preparation of medicines, in particularly as IDO inhibitor medicines, for treating and/or preventing cancers.

BACKGROUND OF THE INVENTION

Indoleamine 2,3-dioxygenase (IDO) is a heme-containing monomeric protein that is widely distributed in tissues other than liver. It is the rate-limiting enzyme in the kynurenine metabolic pathway that catalyzes the oxidative degradation of tryptophan to kynurenine. Tryptophan is an essential amino acid for T cell proliferation and also a precursor for the synthesis of neurotransmitters. If the concentration of tryptophan in the cell microenvironment decreases, the level of kynurenine increases, resulting in T cells arrested in the middle of G1, thereby affecting proliferation, differentiation and activity of T cells.

IDO is expressed at a low level in normal cells, but overexpressed in many tumor tissues, leading to abnormal local tryptophan metabolism and regulatory T cell formation in tumors, which in turn, mediate local T cell immune tolerance in tumors and play an important role in occurrence, development and metastasis of malignant tumors. If the activity of IDO is inhibited, the metabolism of tryptophan around the tumor cells is effectively prevented, which promotes the growth of T cells, thereby enhancing the function of the body's immune system against tumors. Therefore, the development of IDO inhibitors has become a hot area in the search for cancer immunotherapeutic drugs. Preclinical studies have shown that a single dose of IDO1 selective inhibitor INCB-024360 could effectively inhibit the activity of plasma IDO1 in nude mice at the same level as that in IDO-deficient mice, and repeated doses prevented the expansion of CT26 tumors (Koblish et. al, Mol. Cancer Ther., 9(2), 489-98).

IDO inhibitors can also be combined with other anticancer small molecule drugs and immune checkpoint inhibitors, such as CTLA4, PD-1 and PD-L1, to enhance the anticancer efficacy. Combination immunotherapies of immune checkpoint inhibitors with small molecule IDO inhibitors are also in clinical trials, such as indoximod/ipilimumab, epacadostat/pembrolizumab, epacadostat/nivolumab, indoximod/MEDI-4736, etc. Preliminary clinical results showed that the combination of IDO small molecule inhibitor and PD-1 has an additive effect, and has achieved a good disease control rate in the treatment of various tumors, and has fewer side effects than PD-1/CTLA-4, showing a wide range of prospects for tumor immunotherapy (AACR, 2017; ASCO, 2017).

In addition to cancer, IDO is also associated with many other diseases, such as immunosuppression, chronic infection, viral infection, autoimmune diseases or conditions (such as rheumatoid arthritis), neurological or neuropsychiatric diseases or conditions (such as depression), etc. Therefore, IDO inhibitors have great therapeutic values.

Currently, small molecule IDO inhibitor drugs are still in clinical trial stages, including Incyte's INCB-024360 (epacadostat), indoximod from NewLink Genetics, BMS-986205 from BMS and PF-0684003 from Pfizer.

The development of IDO inhibitors has attracted the attention of many biopharmaceutical companies due to its prospects in the treatment of multiple tumors and other diseases by single and combined immunotherapy. A series of patent applications for IDO inhibitors have been published, including WO2006122150A1, WO2011056652A1, WO2013069765A1, WO2014186035A1, WO2015002918A1, WO2016073738A2, WO2016073770A1, WO2016181348A1, WO2016161960A1, WO2017079669A1, etc. However, there is still a need to develop new compounds with better druggability and higher response rates in immunotherapy. Through continuous efforts, the present invention has designed compounds having a structure represented by the general formula (I) and shown that the compounds having such a structure exhibited excellent effects and functions of inhibiting IDO activity.

SUMMARY OF THE INVENTION

The present invention provides compounds of Formula (I), or isomers, prodrugs, stable isotope derivatives, pharmaceutically acceptable salts and mixtures thereof:

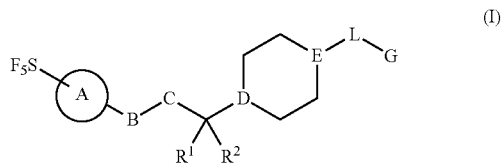

where:

Ring A is a phenyl ring or a 5-6 membered heteroaryl ring;

B is —C(O)— or —NH—;

When B is —C(O)—, C is —NH—; When B is —NH—, C is —C(O)—;

D is N or $CR^3$;

E is N or $CR^4$;

G is an optionally substituted 5-10 membered heteroaryl or 6-10 membered aryl;

L is a bond or —O—;

$R^1$ and $R^2$ are each independently selected from H or an optionally substituted $C_{1-4}$ alkyl, $C_{3-6}$ cycloalkyl or 4-7 membered heterocyclic group; alternatively, $R^1$ and $R^2$ together with the carbon atom to which they are attached form a 3-7 membered ring containing heteroatom(s) optionally selected from O, N and S;

R³ and R⁴ are each independently selected from H, halogen, CN, OH, optionally substituted $C_{1-4}$ alkyl or —O—$C_{1-4}$ alkyl;

R is independently selected from H or optionally substituted $C_{1-4}$ alkyl, $C_{3-6}$ cycloalkyl, 4-7 membered heterocyclic, phenyl or 5-6 membered heteroaryl; two R groups on the same nitrogen atom are optionally combined with the nitrogen atom to which they are attached to form a 4-7 membered heterocyclic ring containing additional heteroatoms optionally selected from O, N and S;

"Optionally substituted" refers to substitution with substituent(s) selected from the group consisting of halogen, —CN, —NO₂, oxo, —SF₅, $C_{1-4}$ alkyl, $C_{3-7}$ cycloalkyl, and 4-7 membered heterocyclic group, phenyl, 5-6 membered heteroaryl, —OR', —NR'R", —C(O)R', —C(O)OR', —C(O)NR'R", —C(O)N(R')OR", —OC(O)R', —OC(O)NR'R", —N(R')C(O)OR", —N(R')C(O)R", —N(R''')C(O)NR'R", —N(R')S(O)₂R", —S(O)$_m$R', —S(O)₂NR'R", where R', R" and R''' are each independently selected from H, $C_{1-4}$ alkyl, $C_{3-7}$ cycloalkyl, halogenated $C_{1-4}$ alkyl, 4-7 membered heterocyclic group, $C_{6-10}$ aryl, 5-10 membered heteroaryl, or R' and R" on the same nitrogen atom are optionally combined with the nitrogen atom to which they are attached to form a 4-7 membered heterocyclic ring containing additional heteroatom(s) optionally selected from O, S and N, and m is 1 or 2.

An embodiment of the present invention relates to compounds of Formula (I), or pharmaceutically acceptable salts, prodrugs, stable isotope derivatives, isomers, and mixtures thereof, where:

Ring A is a phenyl ring or a pyridyl ring;

B is —C(O)— or —NH—;

When B is —C(O)—, C is —NH—; when B is —NH—, C is —C(O)—;

D is N or CR³;

E is N or CR⁴;

G is an optionally substituted 5-10 membered heteroaryl or 6-10 membered aryl;

L is a bond or —O—;

R¹ and R² are each independently selected from H or an optionally substituted $C_{1-4}$ alkyl, $C_{3-6}$ cycloalkyl or 4-7 membered heterocyclic group; alternatively, R¹ and R² together with the carbon atom to which they are attached form a 3-7 membered ring containing heteroatom(s) optionally selected from O, N and S;

R³ and R⁴ are each independently selected from H, halogen, CN, OH, optionally substituted $C_{1-4}$ alkyl or —O—$C_{1-4}$ alkyl;

"Optionally substituted" refers to substitution with substituent(s) selected from the group consisting of halogen, —CN, —NO₂, oxo, —SF₅, $C_{1-4}$ alkyl, $C_{3-7}$ cycloalkyl, and 4-7 membered heterocyclic group, phenyl, 5-6 membered heteroaryl, —OR', —NR'R", —C(O)R', —C(O)OR', —C(O)NR'R", —C(O)N(R')OR", —OC(O)R', —OC(O)NR'R", —N(R')C(O)OR", —N(R')C(O)R", —N(R''')C(O)NR'R", —N(R')S(O)₂R", —S(O)$_m$R', —S(O)₂NR'R", where R', R" and R' are each independently selected from H, $C_{1-4}$ alkyl, $C_{3-7}$ cycloalkyl, halogenated $C_{1-4}$ alkyl, 4-7 membered heterocyclic group, $C_{6-10}$ aryl, 5-10 membered heteroaryl, or R' and R" on the same nitrogen atom are optionally combined with the nitrogen atom to which they are attached to form a 4-7 membered heterocyclic ring containing additional heteroatom(s) optionally selected from O, S and N, and m is 1 or 2.

Another embodiment of the present invention relates to compounds of Formula (II), or pharmaceutically acceptable salts, prodrugs, stable isotope derivatives, isomers and mixtures thereof:

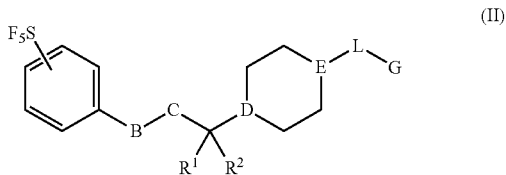

(II)

where:

B is —C(O)— or —NH—;

When B is —C(O)—, C is —NH—; when B is —NH—, C is —C(O)—;

D is N or CR³;

E is N or CR⁴;

G is an optionally substituted 5-10 membered heteroaryl or 6-10 membered aryl;

L is a bond or —O—;

R¹ and R² are each independently selected from H or an optionally substituted $C_{1-4}$ alkyl, $C_{3-6}$ cycloalkyl or 4-7 membered heterocyclic group; alternatively, R¹ and R² together with the carbon atom to which they are attached form a 3-7 membered ring containing heteroatom(s) optionally selected from O, N and S;

R³ and R⁴ are each independently selected from H, halogen, CN, OH, optionally substituted $C_{1-4}$ alkyl or —O—$C_{1-4}$ alkyl;

"Optionally substituted" refers to substitution with substituent(s) selected from the group consisting of halogen, —CN, —NO₂, oxo, —SF₅, $C_{1-4}$ alkyl, $C_{3-7}$ cycloalkyl, and 4-7 membered heterocyclic group, phenyl, 5-6 membered heteroaryl, —OR', —NR'R", —C(O)R', —C(O)OR', —C(O)NR'R", —C(O)N(R')OR", —OC(O)R', —OC(O)NR'R", —N(R')C(O)OR", —N(R')C(O)R", —N(R''')C(O)NR'R", —N(R')S(O)₂R", —S(O)$_m$R', —S(O)₂NR'R", where R', R" and R' are each independently selected from H, $C_{1-4}$ alkyl, $C_{3-7}$ cycloalkyl, halogenated $C_{1-4}$ alkyl, 4-7 membered heterocyclic group, $C_{6-10}$ aryl, 5-10 membered heteroaryl, or R' and R" on the same nitrogen atom are optionally combined with the nitrogen atom to which they are attached to form a 4-7 membered heterocyclic ring containing additional heteroatom(s) optionally selected from O, S and N, and m is 1 or 2.

Another embodiment of the present invention relates to a compound according to any of the preceding embodiments, or pharmaceutically acceptable salt, prodrug, stable isotope derivative, isomer and mixture thereof, where B is —NH— and C is —C(O)—.

Another embodiment of the present invention relates to a compound according to any of the preceding embodiments, where L is a bond.

Another embodiment of the present invention relates to a compound according to any of the preceding embodiments, where D and E are both CH.

Another embodiment of the present invention relates to a compound according to any of the preceding embodiments, where G is a 5-10 membered heteroaryl optionally substituted with halogen, CN, $C_{1-4}$ alkyl or —O—$C_{1-4}$ alkyl group, preferably quinolinyl or pyridyl, more preferably fluoroquinolinyl.

Another embodiment of the invention relates to a compound according to any of the preceding embodiments, where $R^1$ and $R^2$ are each independently selected from H or $C_{1-4}$ alkyl; preferably $R^1$ is $C_{1-4}$ alkyl, $R^2$ is H; more preferably, $R^1$ is methyl and $R^2$ is H.

One embodiment of the present invention relates to a compound according to any of the preceding embodiments of Formula (IIIa)-(IIIc):

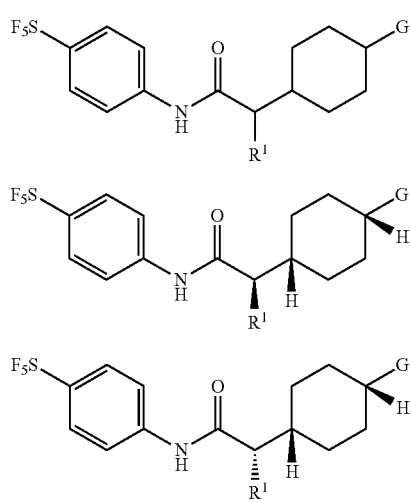

Another embodiment of the present invention relates to a compound according to any of the preceding embodiments of Formula (IV):

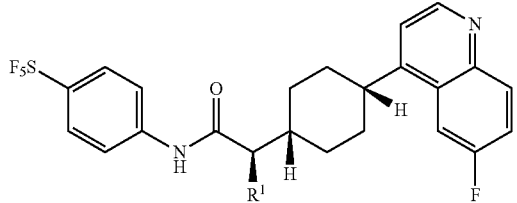

Another embodiment of the present invention relates to a compound of Formula (IV), where $R^1$ is methyl.

An embodiment of the present invention relates to a compound of Formula (I), where the compound is selected from:

| Compound No. | Compound Structure and Name |
|---|---|
| 1. | ![structure] (R)-2-((1s,4S)-4-(6-fluoroquinolin-4-yl)cyclohexyl)-N-(4-(pentafluoro-λ⁶-sulfanyl)phenyl)propanamide |
| 2. | ![structure] (R)-2-((1r,4R)-4-(6-fluoroquinolin-4-yl)cyclohexyl)-N-(4-(pentafluoro-λ⁶-sulfanyl)phenyl)propanamide |
| 3. | ![structure] (R)-2-((1s,4S)-4-(2-methylpyridin-4-yl)cyclohexyl)-N-(4-(pentafluoro-λ⁶-sulfanyl)phenyl)propanamide |
| 4. | ![structure] (R)-N-(4-(pentafluoro-λ⁶-sulfanyl)phenyl)-2-(4-(pyrazolo[1,5-a]pyrimidin-7-yl)cyclohexyl)propanamide |
| 5. | ![structure] 2-(4-(6-fluoroquinolin-4-yl)-1-hydroxycyclohexyl)-N-(4-(pentafluoro-λ⁶-sulfanyl)phenyl)acetamide |
| 6. | ![structure] 2-(4-(6-fluoroquinolin-4-yl)piperazin-1-yl)-N-(4-(pentafluoro-λ⁶-sulfanyl)phenyl)propanamide |

| Compound No. | Compound Structure and Name |
|---|---|
| 7. | 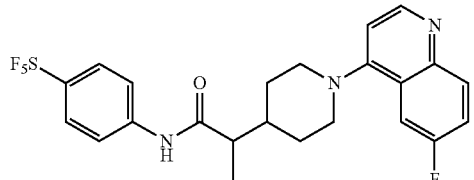<br>2-(1-(6-fluoroquinolin-4-yl)piperidin-4-yl)-N-(4-(pentafluoro-$\lambda^6$-sulfanyl)phenyl)propanamide |
| 8. | 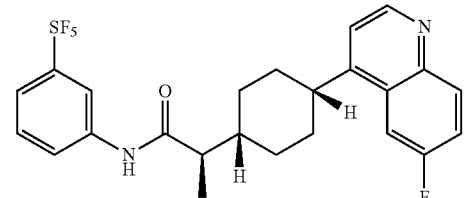<br>(R)-2-((1s,4S)-4-(6-fluoroquinolin-4-yl)cyclohexyl)-N-(3-(pentafluoro-$\lambda^6$-sulfanyl)phenyl)propanamide |
| 9. | 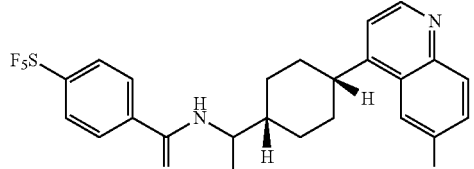<br>N-(1-((1s,4s)-4-(6-fluoroquinolin-4-yl)cyclohexyl)ethyl)-4-(pentafluoro-$\lambda^6$-sulfanyl)benzamide |

Or prodrug, stable isotope derivative, pharmaceutically acceptable salt, isomer and mixture thereof.

The compound of the present invention has a significant inhibitory effect on the activity of IDO in Hela cells, preferably its IC50 is less than 200 nM, and more preferably less than 50 nM.

The compounds of the present invention can be used to treat or prevent related diseases mediated by IDO, including but not limited to cancer, immunosuppression, chronic infection, viral infection, autoimmune diseases or disorders (such as rheumatoid arthritis), nerve or neuropsychiatric diseases or conditions (such as depression), etc. The compounds of the present invention are used to treat or prevent IDO-related tumors, including but not limited to prostate cancer, colon cancer, rectal cancer, membranous adenocarcinoma, cervical cancer, gastric cancer, endometrial cancer, brain cancer, liver cancer, bladder cancer, ovarian cancer, testicular cancer, head cancer, neck cancer, skin cancer (including melanoma and basal cancer), mesothelioma, lymphoma, leukemia, esophageal cancer, breast cancer, muscle cancer, connective tissue cancer, lung cancer (including small cell lung cancer and non-small cell cancer), adrenal cancer, thyroid cancer, renal cancer, bone cancer, glioblastoma, leiomyoma, sarcoma (including Kaposi's sarcoma), choriocarcinoma, skin base cell carcinoma or testicular seminoma. In another aspect, the invention provides a method for treating or preventing IDO-mediated diseases (such as tumors), which comprises administering to a patient in need thereof a therapeutically effective amount of a compound of the present invention or pharmaceutically acceptable salt, prodrug, stable isotope derivative, isomer and mixture thereof, or pharmaceutical composition containing the compound.

Another aspect of the present invention relates to a compound Formula (I), or pharmaceutically acceptable salt, prodrug, stable isotope derivative, isomer, and mixture thereof, as a medicament or for medicinal use, which is useful for treating or preventing IDO-mediated diseases, such as cancer, immunosuppression, chronic infection, viral infection, autoimmune disease or disorder (e.g. rheumatoid arthritis), neurological or neuropsychiatric disease or disorder (e.g. depression), etc.

The present invention further relates to a pharmaceutical composition comprising a compound of the present invention or pharmaceutically acceptable salt, prodrug, stable isotope derivative, isomer and mixtures thereof, and pharmaceutically acceptable carrier(s) and excipient(s).

Another aspect of the present invention relates to a compound of Formula (I) or pharmaceutically acceptable salt, prodrug, stable isotope derivative, isomer, and mixtures thereof, or a pharmaceutical composition in the preparation of medicines, wherein the medicine is used to treat or prevent IDO-mediated diseases, such as tumors and immunosuppression.

Another aspect of this invention relates to a pharmaceutical composition comprising a compound of Formula (I) or pharmaceutically acceptable salt, prodrug, stable isotope derivative, isomer and mixture thereof, with at least one other medicine which is a chemotherapeutic agent, an immune and/or inflammation regulator (such as an immune checkpoint inhibitor), a nerve-related disease regulator, or an anti-infective agent.

According to the present invention, the pharmaceuticals can be in any dosage form, including but not limited to tablets, capsules, solutions, lyophilized formulations, and injectables.

The pharmaceutical formulation of the present invention can be administered in form of a dosage unit containing a predetermined amount of active ingredient. Such a unit may contain, for example, 0.5 mg to 1 g, preferably 1 mg to 700 mg, and more preferably 5 mg to 300 mg of the compound of the present invention, depending on the disease being treated, the method of administration, as well as age, weight, and condition of the patient. Preferred dosage unit formulations are those containing the daily or divided doses as indicated above or their corresponding fractions of the active ingredient. Furthermore, pharmaceutical formulation can be prepared using methods well known in the pharmaceutical field.

The pharmaceutical formulation of the present invention is suitable for administration by any appropriate method, for example, oral (including buccal or sublingual), rectal, nasal, topical (including buccal, sublingual or transdermal), vaginal or parenteral (including subcutaneous, intramuscular, intravenous or intradermal). Such a formulation can be prepared by, for example, formulating the active ingredient with one or more excipients or one or more adjuvants using methods known in the pharmaceutical field.

DETAILED DESCRIPTION OF THE INVENTION

Definitions

Unless otherwise described, the following terms used in the specification and claims of this application have the following meanings.

"$C_{x-y}$" refers to a range of the number of carbon atoms, where x and y are integers, for example, $C_{3-8}$ cycloalkyl stands for cycloalkyl having 3-8 carbon atoms, with 3, 4, 5, 6, 7, or 8 carbon atoms. It should also be understood that "$C_{3-8}$" further includes any sub-range, such as $C_{3-7}$, $C_{3-6}$, $C_{4-7}$, $C_{4-6}$, $C_{5-6}$.

"Alkyl" refers to a saturated linear or branched hydrocarbon substituent containing 1 to 20 carbon atoms, for example, 1 to 8 carbon atoms, 1 to 6 carbon atoms, or 1 to 4 carbon atoms. Unrestricted examples of alkyl include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl and 2-ethylbutyl. Alkyl can be optionally substituted.

"Alkenyl" refers to a straight or branched hydrocarbon substituent containing at least one carbon-carbon double bond and usually 2 to 20 carbon atoms, for example, 2 to 8 carbon atoms, 2 to 6 carbon atoms or 2 to 4 carbon atoms. Unrestricted examples of alkenyl include ethenyl, 1-propenyl, 2-propenyl, 1-butenyl, 2-butenyl, 3-butenyl, 2-methyl-2-propenyl, 1,4-pentadienyl and 1,4-butadienyl. Alkenyl can be optionally substituted.

"Alkynyl" refers to a straight or branched hydrocarbon substituent containing at least one carbon-carbon triple bond and typically 2 to 20 carbon atoms, for example, 2 to 8 carbon atoms, 2 to 6 carbon atoms or 2 to 4 carbon atoms. Unrestricted examples of alkynyl include ethynyl, 1-propynyl, 2-propynyl, 1-butynyl, 2-butynyl and 3-butynyl. Alkynyl can be optionally substituted.

"Alkylene" refers to a saturated straight or branched hydrocarbon divalent substituent containing from 1 to 20 carbon atoms, for example, 1 to 8 carbon atoms, 1 to 6 carbon atoms or 1 to 4 carbon atoms. Unrestricted examples of alkylene include —CH$_2$—, —CH(CH$_3$)—, —CH$_2$CH$_2$—, CH$_2$CH$_2$CH$_2$—, —CH$_2$CH$_2$CH$_2$CH$_2$— and —CH$_2$CH(CH$_3$)CH$_2$—. Alkylene can be optionally substituted.

"Cycloalkyl" refers to a saturated cyclic hydrocarbon substituent containing from 3 to 14 annular carbon atoms. Cycloalkyl can be a single carbocyclic ring substituent, usually containing 3 to 7 carbon atoms, preferably 3 to 6 carbon atoms. Unrestricted examples of monocyclic cycloalkyl include but are not limited to cyclopropyl, cyclobutyl, cyclopentyl, cyclohexyl and cycloheptyl. Cycloalkyl can also be a substituent of two or three mono carbon rings that are fused together, such as decahydronaphthyl. Cycloalkyl can be optionally substituted.

"Heterocyclyl" or "heterocycle" refers to a saturated or partially unsaturated monocyclic or polycyclic group containing 3 to 20 annular atoms, for example, 3 to 14, 3 to 12, 3 to 3 10, 3 to 8, 3 to 6, or 5 to 6 annular atoms, in which one or more of the annular atoms are selected from nitrogen, oxygen or S(O)$_m$ (where m is an integer from 0 to 2), but does not include the ring portion of —OO—, —OS— or —SS— in the ring structure, and the rest are carbon. Preferably, it can have 3 to 12 annular atoms, more preferably 3 to 10 annular atoms and 4 to 7 annular atoms, most preferably 5 or 6 annular atoms, in which 1 to 4 atoms are heteroatoms, more preferably 1 to 3 are heteroatoms, most preferably 1 to 2 are heteroatoms. Unrestricted examples of monocyclic heterocyclyl include but are not limited to pyrrolidinyl, piperidinyl, piperazinyl, pyranyl, morpholinyl, thiomorpholinyl, homopiperazinyl and azetidinyl. Polycyclic heterocyclyl includes fused, bridged or spiro polycyclic heterocycles. Heterocyclyl or heterocycle can be optionally substituted.

"Aryl" or "aryl ring" refers to an aromatic monocyclic or fused polycyclic group containing 6 to 14 carbon atoms, preferably 6 to 10 members, such as phenyl and naphthyl, most preferably phenyl. The aryl ring can be fused to a heteroaryl, heterocyclyl or cycloalkyl ring. Unrestricted examples include:

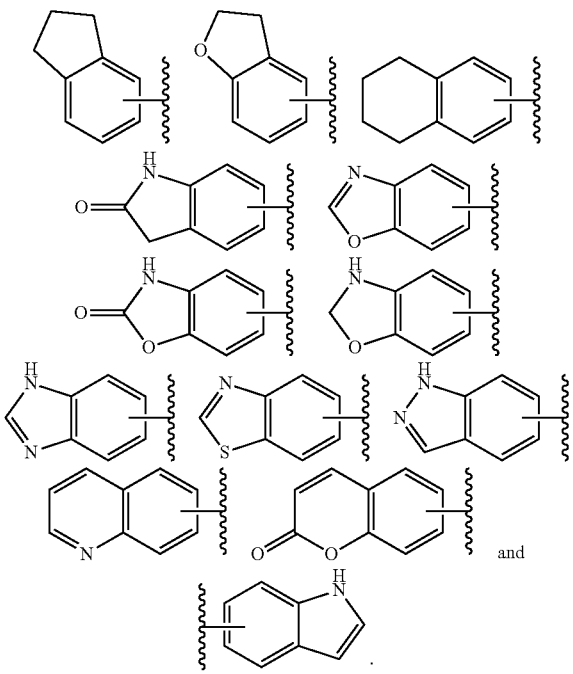

The aryl ring can be optionally substituted.

"Heteroaryl" or "heteroaryl ring" refers to an aromatic group containing 5 to 14 ring atoms, of which 1 to 4 annular atoms are heteroatoms selected from oxygen, sulfur and nitrogen. Preferably heteroaryl is 5 to 10 membered. More preferably, heteroaryl is 5- or 6-membered, such as furyl, thienyl, pyridyl, pyrrolyl, N-alkylpyrrolyl, pyrimidinyl, pyrazinyl, pyrazolyl, imidazolyl, tetrazolyl, oxazolyl, isoxazolyl, thiazolyl, isothiazolyl, etc. The heteroaryl ring can be fused to an aryl, heterocyclic or cycloalkyl ring. Unrestricted examples include:

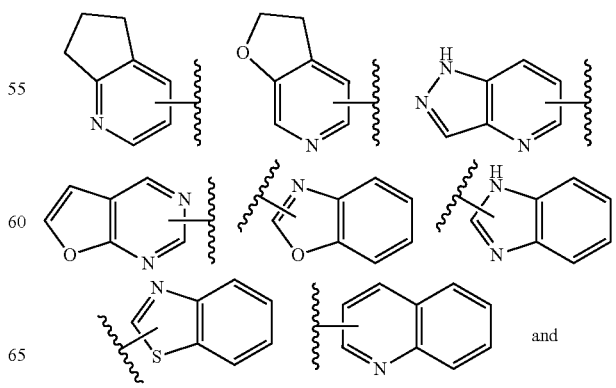

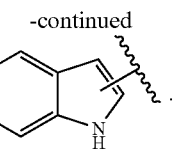

Heteroaryl can be optionally substituted.

"Halogen" refers to fluoro, chloro, bromo or iodo.

"Cyano" refers to —CN.

"Optional" or "optionally" implies that the subsequently described event or environment may, but may not, occur, including the occurrence or non-occurrence of the event or environment. For example, "heterocyclyl optionally substituted by an alkyl group" implies that an alkyl group may be, but not be necessarily present, and the description includes the case where the heterocyclic group is substituted with an alkyl group and the case where the heterocyclic group is not substituted with an alkyl group.

"Substituted" refers to that one or more hydrogen atoms in a group, preferably 5, more preferably 1 to 3 hydrogen atoms, are independently replaced with a corresponding number of substituents. It goes without saying that the substituents are only in their possible chemical positions, and those skilled in the art can determine a substitution that may or may not be possible without making much effort (by experiment or theory). For example, an amino or hydroxyl group having a free hydrogen may be unstable when connected to a carbon atom having an unsaturated bond (e.g. olefinic). The substituents include but are not limited to halogen, —CN, —NO$_2$, oxo, —SF$_5$, C$_{1-4}$ alkyl, C$_{3-7}$ cycloalkyl, and 4-7 membered heterocyclic group, phenyl, 5-6 membered heteroaryl, —OR', —NR"R", —C(O)R', —C(O)OR', —C(O)NR'R", —C(O)N(R')OR", —OC(O)R', —OC(O)NR'R", —N(R')C(O)OR", —N(R')C(O)R", —N(R''')C(O)NR'R", —N(R')S(O)$_2$R", —S(O)$_m$R' (m is 1 or 2), —S(O)$_2$NR'R", wherein R', R" and R''' are each independently selected from H, C$_{1-4}$ alkyl, C$_{3-7}$ cycloalkyl, halogenated C$_{1-4}$ alkyl, 4-7 membered heterocyclic group, C$_{6-10}$ aryl, 5-10 membered heteroaryl, or R' and R" on the same nitrogen atom are optionally combined with the nitrogen atom to which they are attached to form a 4-7 membered heterocyclic ring containing additional heteroatoms optionally selected from O, S and N.

"Isomers" refer to compound that have the same molecular formula but the nature or order of their atomic bonding or spatial arrangement is different. Isomers with different arrangement of their atoms in space are called "stereoisomers". Stereoisomers include optical isomers, geometric isomers and conformational isomers.

The compounds of the present invention can exist in form of optical isomers. The optical isomers are of the "R" or "S" configuration according to the configuration of the substituents around the chiral carbon atom. Optical isomers include enantiomers and diastereomers. Methods for preparing and isolating optical isomers are known in the art.

The compounds of the present invention can also have geometric isomers, resulting from the distribution of substituents around carbon-carbon double bonds, carbon-nitrogen double bonds, cycloalkyl or heterocyclic groups. The substituents around a carbon-carbon double bond or a carbon-nitrogen bond are designated as a Z or E configuration, and the substituents around a cycloalkyl or heterocycle are designated as a cis or trans configuration.

The compounds of the present invention can also exhibit tautomerism, such as keto-enol tautomerism.

It is to be understood that the present invention includes any tautomeric or stereoisomeric forms and mixtures thereof and is not limited to any one of the tautomeric or stereoisomeric forms used in the nomenclature or chemical structural formula.

The present invention includes all isotopes of atoms occurring in the compounds of the present invention. Isotopes include those atoms that have the same atomic number but different mass numbers. Examples of isotopes suitable for incorporation into the compounds of the present invention are isotopes of hydrogen, carbon, nitrogen, oxygen, phosphorus, sulfur, fluorine and chlorine, for example but not limited to $^{2}$H, $^{3}$H, $^{13}$C, $^{14}$C, $^{15}$N, $^{18}$O, $^{17}$O, $^{31}$P, $^{32}$P, $^{35}$, $^{18}$F and $^{36}$Cl. Isotopically labeled compounds of the present invention can generally be prepared by conventional techniques known to those skilled in the art or by methods similar to those described in the embodiments using appropriate isotopically labeled reagents instead of non-isotopically labeled reagents. Such compounds have a variety of potential uses, for example, as standards and reagents for the determination of biological activity. In the case for stable isotopes, such compounds have the potential to beneficially alter biological, pharmacological or pharmacokinetic properties.

The compounds of the invention can also be administered in form of prodrugs. Prodrugs refers to derivatives that are converted to the biologically active compounds of the present invention under the physiological condition in vivo, for example, by oxidation, reduction, or hydrolysis (each of which occurs with or without the participation of an enzyme). Examples of a prodrug are a compound of the present invention of which an amino group is acylated, alkylated or phosphorylated, such as eicosanoylamino, alanylamino, pivaloyloxymethylamino, a hydroxy group is acylated, alkylated, phosphorylated or converted to borate, such as acetoxy, palmitoyloxy, pivaloyloxy, succinyloxy, fumaroyloxy, alanyloxy, a carboxyl group is esterified or amidated, or a sulfhydryl group forms a disulfide bridge with a carrier molecule, such as a peptide, that selectively delivers the drug to the target and/or to the cytosol of the cell. Prodrugs can be prepared from the compounds of the present invention according to known methods.

"Pharmaceutically acceptable salt" refers to a salt made of a pharmaceutically acceptable base or acid, including an inorganic base or acid, and an organic base or acid. Where the compounds of the invention contain one or more acidic or basic groups, the present invention also relates to their corresponding pharmaceutically acceptable salts. Therefore, the compounds of the present invention containing acidic groups can exist in form of salts, for example, as alkali metal salts, alkaline earth metal salts or as ammonium salts. More precisely examples of such salts include sodium salts, potassium salts, calcium salts, magnesium salts or salts with ammonia or organic amines such as ethylamine, ethanolamine, triethanolamine or amino acids. The compounds of the present invention containing basic groups can exist in form of salts as inorganic or organic acid salts. Examples of suitable acids include hydrochloric acid, hydrobromic acid, phosphoric acid, sulfuric acid, nitric acid, methanesulfonic acid, p-toluenesulfonic acid, naphthalene disulfonic acid, oxalic acid, acetic acid, tartaric acid, lactic acid, salicylic acid, benzoic acid, formic acid, propylene Acid, pivalic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid and other acids known to those skilled in the art. If the compounds of the present invention contain both acidic and basic groups in the molecule, the present invention further includes internal salts in addition to the mentioned salt forms. Each salt can be obtained by conventional methods known to those skilled in the art, for example, by mixing a compound of the present invention with an organic or inorganic acid or base in a solvent or dispersant, or by anion or cation exchange with another salt.

"Pharmaceutical composition" refers to a combination containing one or more compounds of the present invention, or pharmaceutically acceptable salt, prodrug, stable isotope derivative, isomer, or mixture thereof, and other components such as pharmaceutically acceptable carriers and excipients. The use of the pharmaceutical composition is to promote the administration to the organism, by facilitating the absorption of the active ingredient and thereby exerting the biological activity.

When "compounds" or "compounds of the present invention" are mentioned in the present invention, all compound forms are included, such as pharmaceutically acceptable salts, prodrugs, stable isotope derivatives, isomers as well as mixtures thereof.

"Tumor" includes benign and malignant tumors (e.g. cancer).

"Therapeutically effective amount" refers to an amount of a compound of the present invention that can effectively inhibit the function of IDO and/or treat or prevent a disease.

Synthetic Methods

The present invention further provides a method for preparing the compounds. The compounds of the present invention as shown in Formula (I) can be prepared by the following exemplary methods and embodiments, but these methods and embodiments should not be considered as limitations to the scope of the present invention in any ways. The compounds of the present invention can also be synthesized by synthetic techniques known to those skilled in the art, or a combination of methods known in the art and described in the present invention. The product obtained in each step of the reaction is isolated by separation techniques known in the art, including but not limited to extraction, filtration, distillation, crystallization, chromatographic separation. The starting materials and chemical reagents used for the synthesis can be made based on the literature (from SciFinder) or purchased.

The pentafluorosulfanyl-substituted amide compounds shown in Formula (I) of the present invention can be synthesized by the route described in Method A: firstly, the intermediate acid A2 is converted into an acid chloride or activated with an amide formation reagent, then coupled with a chemicals containing pentafluorosulfanyl-substituted (hetero)aryl aniline A1 to afford the targeted amide product A3.

Method A

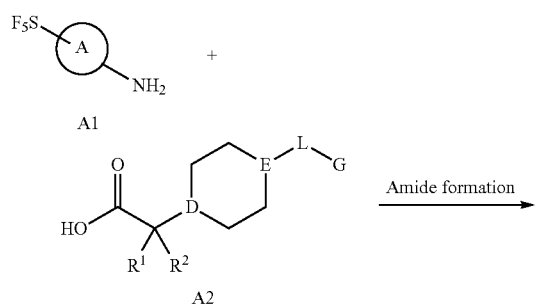

The pentafluorosulfanyl-substituted amide compound shown in Formula (I) of the present invention can also be synthesized by the route described in Method B: (hetero)aryl carboxylic acid B1 containing a pentafluorosulfanyl substituent is converted into an acid chloride which is then coupled with the intermediate amine B2 to afford the targeted amide compound B3.

Method B

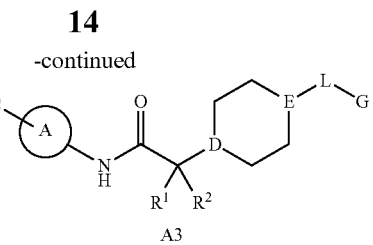

The intermediate acid A2 can be synthesized by the route described in Method C: ketone C1 reacts with trifluoromethanesulfonic anhydride under basic conditions to form hydrocarbon alkenyl trifluoromethanesulfonate C2; C3 is obtained by Suzuki coupling reaction between C2 and a borate or boronic acid, G-B(OR)$_2$, followed by reduction to C4 under hydrogenation; C4 is then substituted with one equivalent of a halogenated alkane, or further substituted by a second equivalent of the halogenated alkane to give C5; finally acid A2 is obtained via hydrolysis under alkali catalysis.

Method C

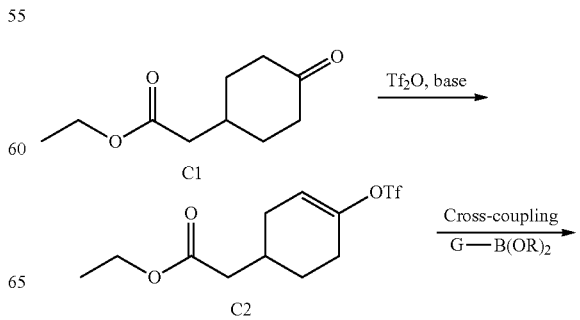

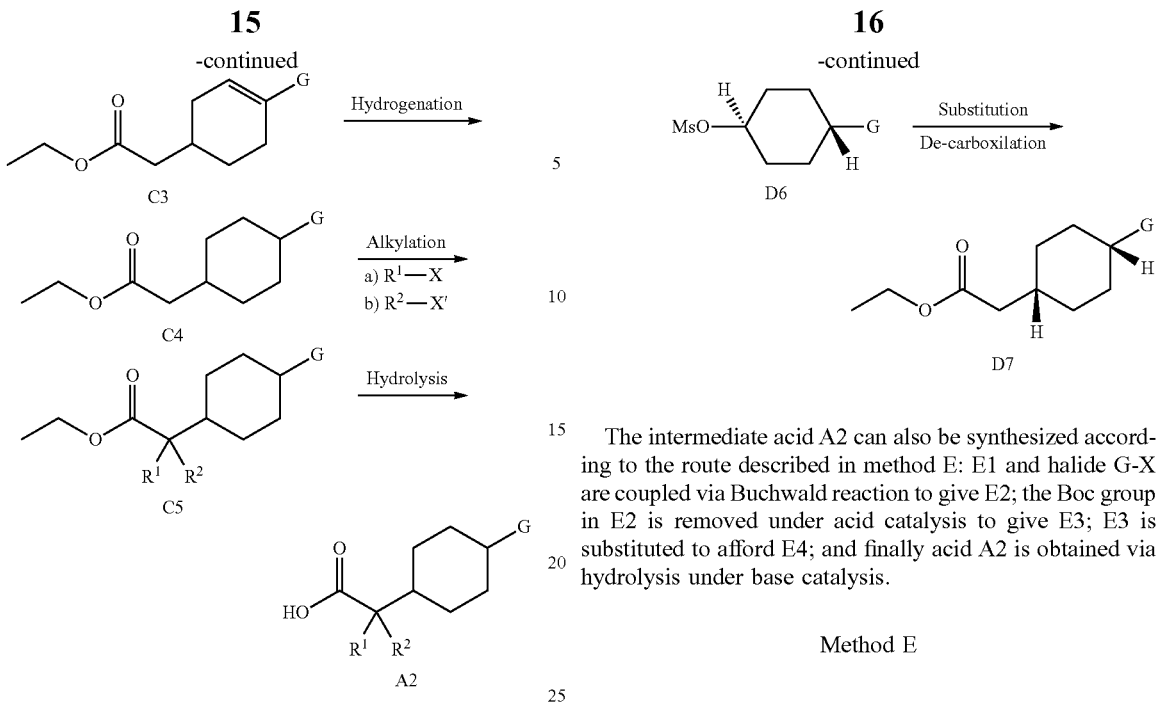

The intermediate ester D7 can be synthesized according to the route described in Method D: ketone D1 reacts with N-phenylbis(trifluoromethanesulfonyl)imide under basic conditions to produce hydrocarbon alkenyl trifluoromethanesulfonate D2; D2 is coupled with a borate or boronic acid, G-B(OR)$_2$ via Suzuki reaction to give D3 which is then hydrogenated, followed by deprotection to produce ketone D4; ketone D4 is reduced to mainly trans-alcohol D5; alcohol D5 is converted to the mesylate ester D6 under basic conditions; D6 is substituted by the sodium salt of di-tert-butyl malonate to form a cis intermediate, which is then deprotected and decarboxylated under acidic conditions to give a cis intermediate ester D7.

Method D

The intermediate acid A2 can also be synthesized according to the route described in method E: E1 and halide G-X are coupled via Buchwald reaction to give E2; the Boc group in E2 is removed under acid catalysis to give E3; E3 is substituted to afford E4; and finally acid A2 is obtained via hydrolysis under base catalysis.

Method E

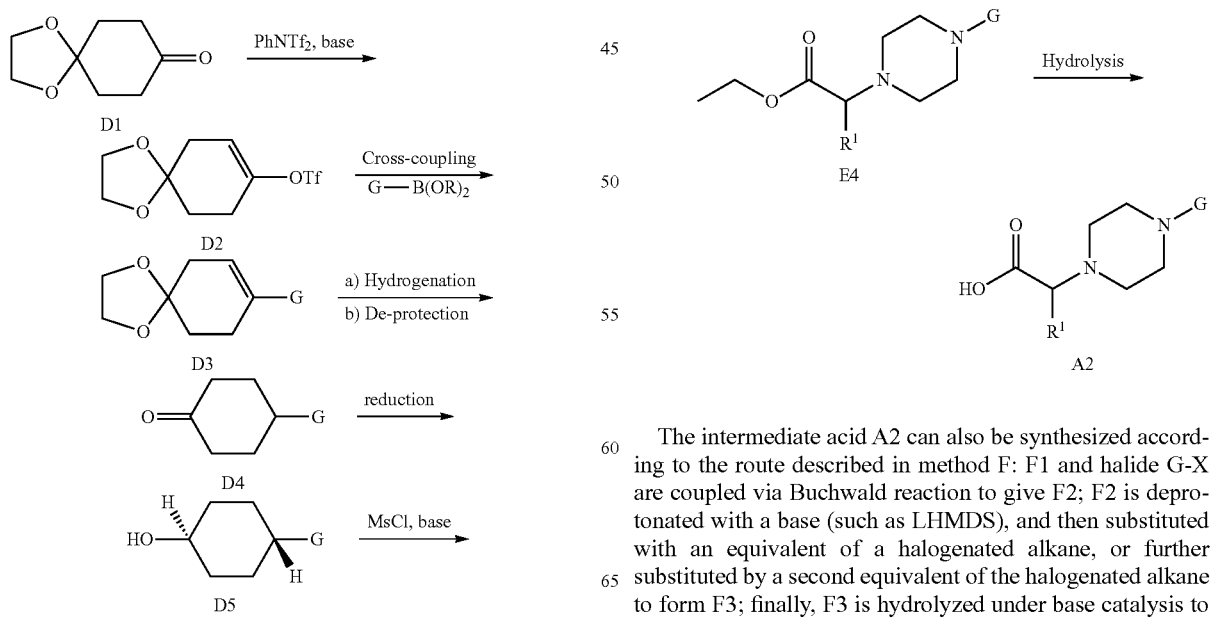

The intermediate acid A2 can also be synthesized according to the route described in method F: F1 and halide G-X are coupled via Buchwald reaction to give F2; F2 is deprotonated with a base (such as LHMDS), and then substituted with an equivalent of a halogenated alkane, or further substituted by a second equivalent of the halogenated alkane to form F3; finally, F3 is hydrolyzed under base catalysis to afford acid A2.

Method F

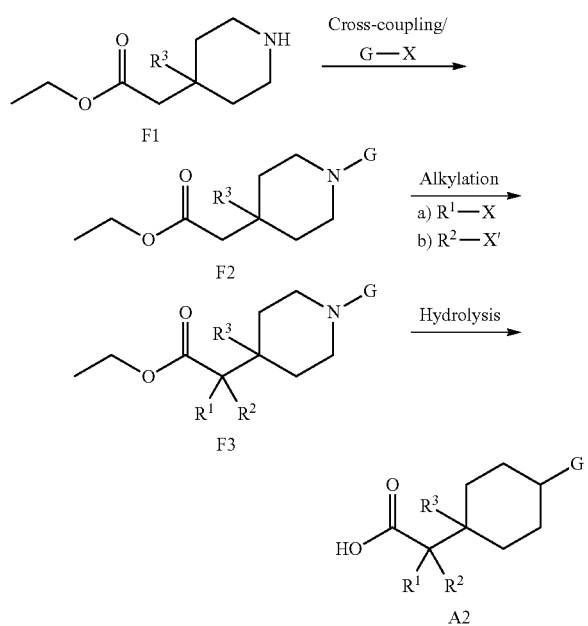

The intermediate acid A2 can also be synthesized according to the route described in Method G: G1 is reduced to G2 by a boron reagent; G2 undergoes nucleophilic substitution reaction or Mitsunobu reaction to give G3; G3 is hydrolyzed under alkali catalysis to afford acid A2.

Method G

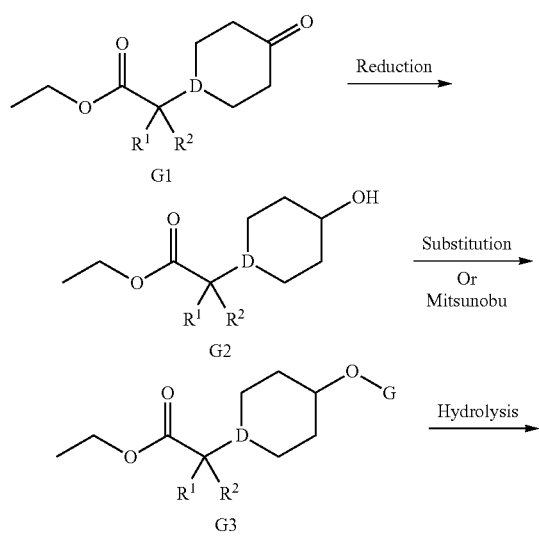

The chiral intermediate acid A2 can be synthesized according to the route described in method H: acid H1 firstly forms a mixed anhydride with an acid chloride (such as pivaloyl chloride) under base catalysis, substituted by (R)-chiral auxiliary (such as lithium salt of (R)-4-benzyloxazolidin-2-one) to form (R)—H2; (R)—H2 is deprotonated with a strong base, and then reacted with methyl iodide to give (R)—H3; (R)-A2 is finally obtained via hydrolysis under alkali catalysis. If a (S)-chiral auxiliary agent is used (such as (S)-4-benzyloxazolidin-2-one), then (S)-A2 is obtained.

Method H

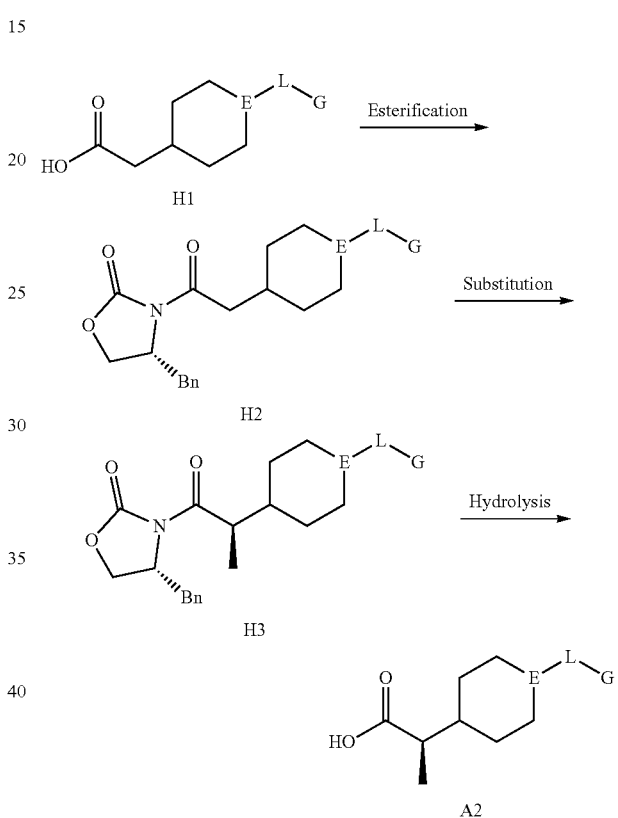

the intermediate amine B2 can be synthesized according to the route described in Method I: I2 is obtained from I1 by similar methods of C and G; I2 is reduced to alcohol by LAH, and then oxidized with Dess-Martin oxidant to form aldehyde I3; I3 reacts with a Grignard reagent to form I4; I4 produces I5 through a Mitsunobu reaction; finally, deprotection of I5 gives amine B2.

Method I

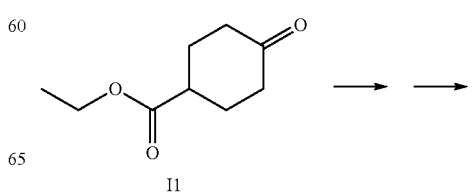

19

-continued

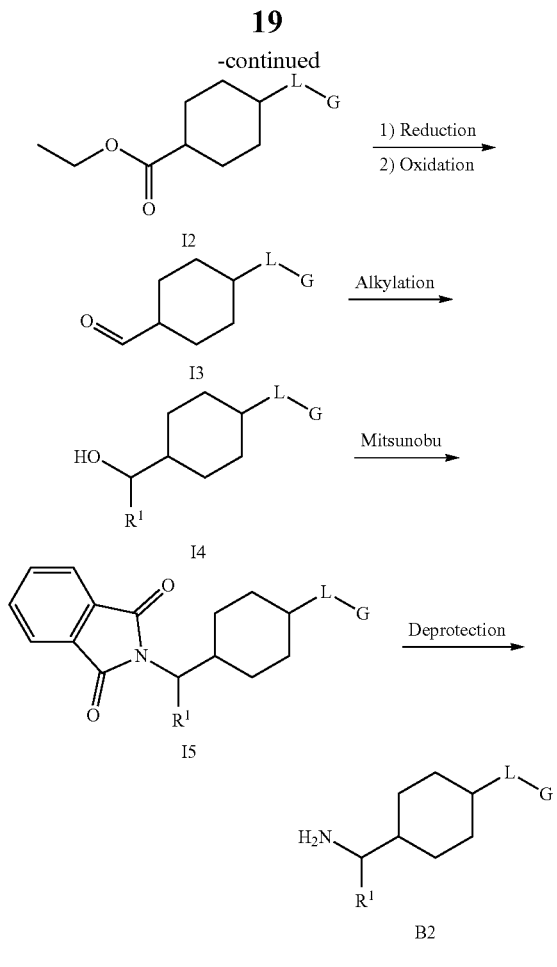

EXAMPLES

The compound structure was determined by nuclear magnetic resonance (NMR) or mass spectrometry (MS). NMR was measured by Bruker AVANCE-400, the solvent for the determination was deuterated dimethyl sulfoxide (DMSO-d6), deuterated chloroform (CDCl$_3$), deuterated methanol (CD$_3$OD), the internal standard was tetramethylsilane (TMS), and chemical shifts were given in unit of $10^{-6}$ (ppm).

MS was measured using an Agilent SQD (ESI) mass spectrometer (Agilent, model: 6120).

HPLC was run using an Agilent 1260 DAD high pressure liquid chromatograph (column: Poroshell120 EC-C18, 50×3.0 mm, 2.7 μm) or a Waters Arc high pressure liquid chromatograph (column: Sunfire C18, 150×4.6 mm, 5 μm).

Qingdao Ocean GF254 silica gel plate was used for thin-layer chromatography. The specification of silica gel plate used for thin-layer chromatography (TLC) was 0.15 mm 0.2 mm. The specification for thin layer chromatography separation and purification was 0.4 mm 0.5 mm.

Qingdao Ocean 200-300 mesh silica gel was used as the carrier for column chromatography.

The known starting materials used for the present invention can be synthesized according to methods known in the art, or can be purchased from ABCR GmbH & Co. KG, Acros Organics, Aldrich Chemical Company, Accela ChemBio Inc., Beijing Ouhe Technology Co., etc.

Unless otherwise specified, the reactions in the examples were carried out under an argon or nitrogen atmosphere.

An argon or nitrogen atmosphere refers to that the reaction flask was connected to an argon or nitrogen balloon of about 1 L volume.

20

A hydrogen atmosphere refers to that the reaction bottle was connected to a hydrogen balloon of about 1 L volume.

The hydrogenation reaction is usually carried out by evacuation and filling with hydrogen for three times.

CEM Discover-SP microwave reactor was used for microwave reactions.

Unless otherwise specified in the examples, the reaction temperature was room temperature, and the temperature range was 20-30° C.

The reaction progress in the examples was monitored by Agilent LC-MS (1260/6120). The reaction progress in the examples was also monitored by thin layer chromatography (TLC), and the eluent system used was A: dichloromethane and methanol system; B: petroleum ether and ethyl acetate system, and the volume ratio of the solvents was adjusted based on polarity of the compound.

The eluent system used for compound purification by column chromatography and thin layer chromatography included A: dichloromethane and methanol systems; B: petroleum ether and ethyl acetate system, and the volume ratio of the solvents was adjusted based on polarity of the compound. It could also be adjusted by adding a small amount of triethylamine, and acidic or alkaline reagents. The compounds can also be purified by using Waters mass spectrometry-guided automated preparation system (mass spectrometer detector: SQD2), with appropriate acetonitrile/water (containing 0.1% trifluoroacetic acid) or acetonitrile/water (containing 0.05% ammonia) gradient elution according to the polarity of the compound. The reversed-phase high-pressure column (XBridge-C18, 19×150 mm, 5 μm) was eluted at a flow rate of 20 mL/min.

Example 1

(R)-2-((1s,4S)-4-(6-fluoroquinolin-4-yl)cyclohexyl)-N-(4-(pentafluoro-λ$^6$-sulfanyl)phenyl)propanamide

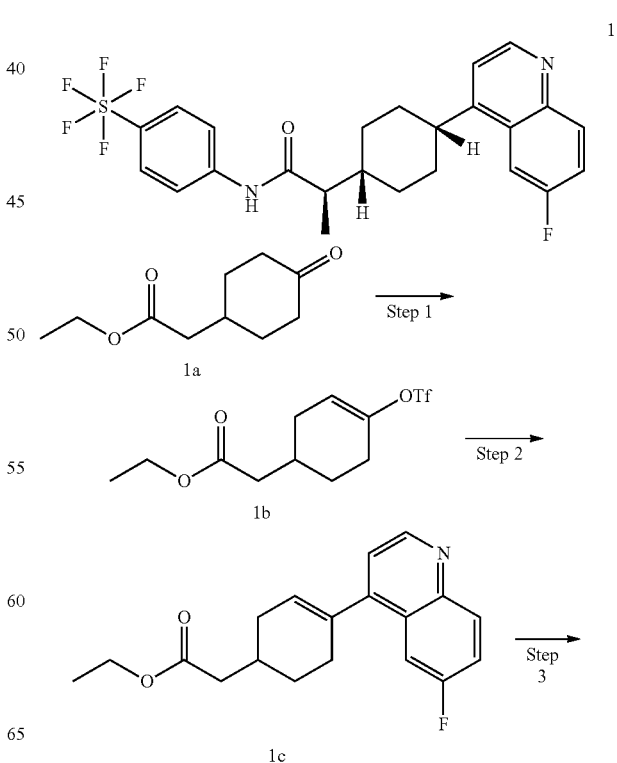

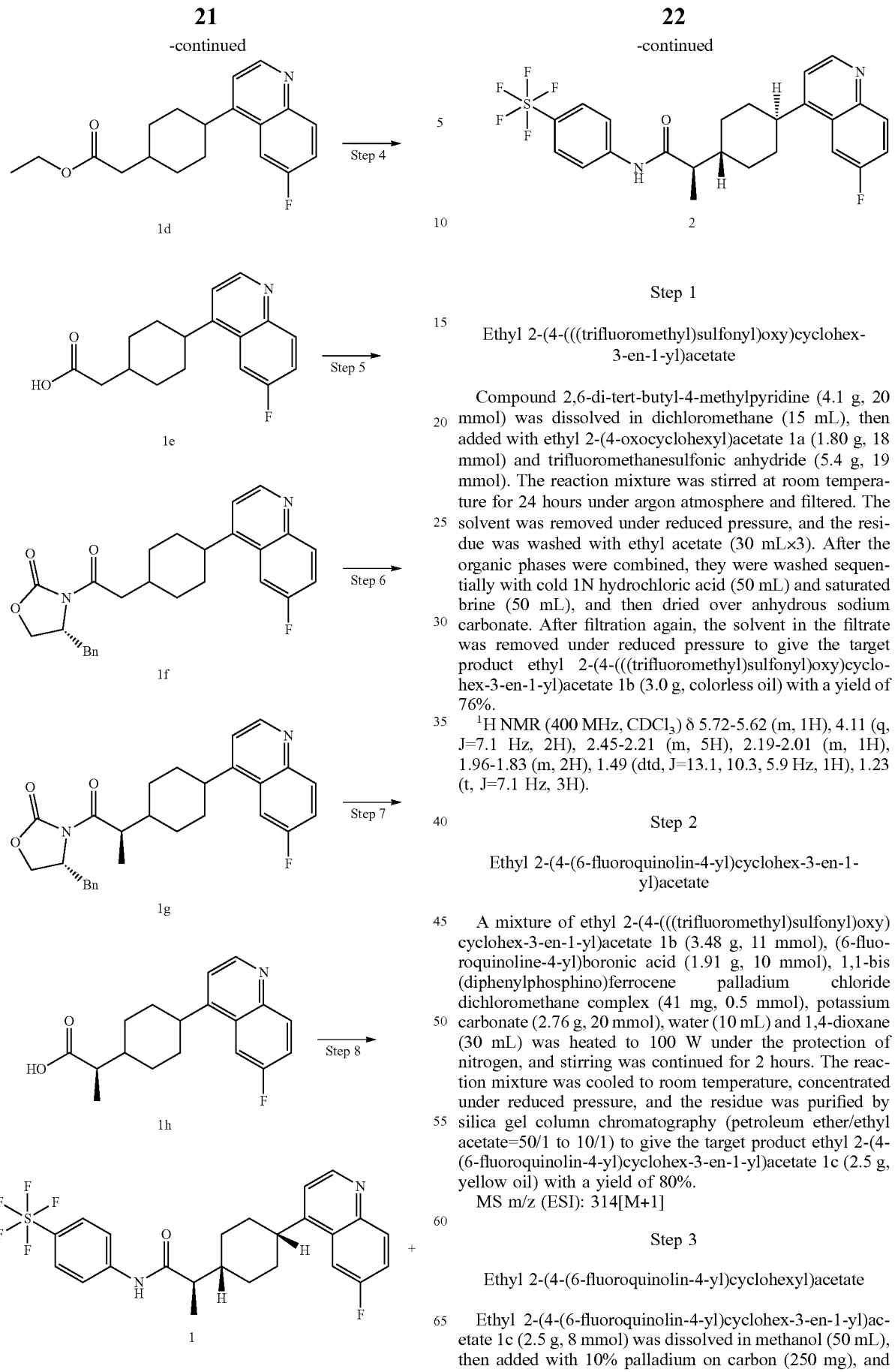

Step 1

Ethyl 2-(4-(((trifluoromethyl)sulfonyl)oxy)cyclohex-3-en-1-yl)acetate

Compound 2,6-di-tert-butyl-4-methylpyridine (4.1 g, 20 mmol) was dissolved in dichloromethane (15 mL), then added with ethyl 2-(4-oxocyclohexyl)acetate 1a (1.80 g, 18 mmol) and trifluoromethanesulfonic anhydride (5.4 g, 19 mmol). The reaction mixture was stirred at room temperature for 24 hours under argon atmosphere and filtered. The solvent was removed under reduced pressure, and the residue was washed with ethyl acetate (30 mL×3). After the organic phases were combined, they were washed sequentially with cold 1N hydrochloric acid (50 mL) and saturated brine (50 mL), and then dried over anhydrous sodium carbonate. After filtration again, the solvent in the filtrate was removed under reduced pressure to give the target product ethyl 2-(4-(((trifluoromethyl)sulfonyl)oxy)cyclohex-3-en-1-yl)acetate 1b (3.0 g, colorless oil) with a yield of 76%.

$^1$H NMR (400 MHz, CDCl$_3$) δ 5.72-5.62 (m, 1H), 4.11 (q, J=7.1 Hz, 2H), 2.45-2.21 (m, 5H), 2.19-2.01 (m, 1H), 1.96-1.83 (m, 2H), 1.49 (dtd, J=13.1, 10.3, 5.9 Hz, 1H), 1.23 (t, J=7.1 Hz, 3H).

Step 2

Ethyl 2-(4-(6-fluoroquinolin-4-yl)cyclohex-3-en-1-yl)acetate

A mixture of ethyl 2-(4-(((trifluoromethyl)sulfonyl)oxy)cyclohex-3-en-1-yl)acetate 1b (3.48 g, 11 mmol), (6-fluoroquinoline-4-yl)boronic acid (1.91 g, 10 mmol), 1,1-bis(diphenylphosphino)ferrocene palladium chloride dichloromethane complex (41 mg, 0.5 mmol), potassium carbonate (2.76 g, 20 mmol), water (10 mL) and 1,4-dioxane (30 mL) was heated to 100 W under the protection of nitrogen, and stirring was continued for 2 hours. The reaction mixture was cooled to room temperature, concentrated under reduced pressure, and the residue was purified by silica gel column chromatography (petroleum ether/ethyl acetate=50/1 to 10/1) to give the target product ethyl 2-(4-(6-fluoroquinolin-4-yl)cyclohex-3-en-1-yl)acetate 1c (2.5 g, yellow oil) with a yield of 80%.

MS m/z (ESI): 314[M+1]

Step 3

Ethyl 2-(4-(6-fluoroquinolin-4-yl)cyclohexyl)acetate

Ethyl 2-(4-(6-fluoroquinolin-4-yl)cyclohex-3-en-1-yl)acetate 1c (2.5 g, 8 mmol) was dissolved in methanol (50 mL), then added with 10% palladium on carbon (250 mg), and stirred at room temperature for 2 hours under hydrogen atmosphere. The mixture was filtered and the filtrate was concentrated under reduced pressure to give the target product ethyl 2-(4-(6-fluoroquinolin-4-yl)cyclohexyl)acetate 1d (2.2 g, light yellow solid) with a yield of 88%.

MS m/z (ESI): 316[M+1]

Step 4

2-(4-(6-Fluoroquinolin-4-yl)cyclohexyl)acetic acid

Ethyl 2-(4-(6-fluoroquinolin-4-yl)cyclohexyl)acetate 1d (3.15 g, 10 mmol), lithium hydroxide monohydrate (630 mg, 15 mmol) and tetrahydrofuran (20 mL) were mixed, then added with water (10 mL). The reaction mixture was heated to 50□ and stirred for 5 hours. After the reaction was completed, the solvents were removed under reduced pressure, and the residue was purified by reversed-phase high-performance liquid chromatography to obtain the target product 2-(4-(6-fluoroquinolin-4-yl)cyclohexyl)acetic acid 1e (2.53 g, white solid) with a yield of 88%.

MS m/z (ESI): 288[M+1]

Step 5

(R)-4-Benzyl-3-(2-(4-(6-fluoroquinolin-4-yl)cyclohexyl)acetyl)oxazolidin-2-one

Compound 2-(4-(6-fluoroquinolin-4-yl)cyclohexyl)acetic acid 1e (287 mg, 1 mmol) was dissolved in anhydrous tetrahydrofuran (10 mL), then added with triethylamine (202 mg, 2 mmol) under nitrogen atmosphere. After cooled to −78□, the mixture was added with pivaloyl chloride (150 mg, 1.25 mmol) dropwise. After stirring at 0 for one hour, a suspension was obtained for future use.

(R)-4-Benzyloxazolidin-2-one (230 mg, 1.3 mmol) was dissolved in anhydrous tetrahydrofuran (10 mL) and cooled to −78□, then a solution of n-butyllithium in hexane (2.5M, 0.52 mL, 1.3 mmol) was added dropwise under nitrogen atmosphere. After stirring at −78□ for 15 minutes, the temperature was gradually raised to 0□ and the mixture was stirred for 15 minutes. The resulting pale-yellow solution was then cooled to −78□ again for future use.

The above suspension was cooled to −78□, then added with the pale-yellow solution cooled to −78□. The reaction mixture was gradually warmed to room temperature and stirred for another 3 hours. The reaction mixture was added with saturated ammonium chloride solution (10 mL) and extracted with ethyl acetate (50 mL×3). The organic phases were combined and washed with saturated brine (20 mL×2). After drying over anhydrous sodium sulfate and filtering, the solvent in the filtrate was removed under reduced pressure, and the residue was purified by silica gel column chromatography (petroleum ether/ethyl acetate=1/1 to 1/5) to give the target product (R)-4-Benzyl-3-(2-(4-(6-fluoroquinolin-4-yl)cyclohexyl)acetyl)oxazolidin-2-one if (350 mg, colorless oil) with a yield of 78%.

MS m/z (ESI): 447[M+1]

Step 6

(R)-4-benzyl-3-((R)-2-(4-(6-fluoroquinolin-4-yl)cyclohexyl)propanoyl)oxazolidin-2-one Compound (R)-4-Benzyl-3-(2-(4-(6-fluoroquinolin-4-yl)cyclohexyl)acetyl)oxazolidin-2-one if (223 mg, 0.5 mmol) was dissolved in anhydrous tetrahydrofuran (5 mL), cool to −50□, then added with a solution of sodium bis(trimethylsilyl)amide in tetrahydrofuran (2 M, 0.3 mL, 0.6 mmol). After stirring for 10 minutes, iodomethane (99.4 mg, 0.7 mmol) was added and stirring was continued for 2 hours. After quenched with saturated ammonium chloride solution (10 mL), the mixture was extracted with ethyl acetate (20 mL×3). The organic phases were combined, washed with saturated brine (20 mL), dried over anhydrous sodium sulfate and filtered. The solvent in the filtrate was removed under reduced pressure, and the residue was purified by silica gel column chromatography (petroleum ether/ethyl acetate=1/1 to 1/5) to give the target product (R)-4-benzyl-3-((R)-2-(4-(6-fluoroquinolin-4-yl)cyclohexyl)propanoyl)oxazolidin-2-one 1g (180 mg, colorless oil) with a yield of 78%.

MS m/z (ESI): 461[M+1]

Step 7

(R)-2-(4-(6-fluoroquinolin-4-yl)cyclohexyl)propanoic acid (R)-4-benzyl-3-((R)-2-(4-(6-fluoroquinolin-4-yl)cyclohexyl)propanoyl)oxazolidin-2-one 1g (500 mg, 1.1 mmol), water (10 mL) and tetrahydrofuran (10 mL) were mixed, cooled to 0□, then added with 35% hydrogen peroxide aqueous solution (0.5 mL) and lithium hydroxide monohydrate (73 mg, 1.74 mmol). After gradually warming to room temperature, stirring was continued for 1 hour. The mixture was re-cooled to 0□ and slowly added with saturated sodium sulfite solution to quench the reaction. The mixture was extracted with ethyl acetate (20 mL×3). After the organic phases were combined, the solvent was removed under reduced pressure, and the residue was purified by silica gel column chromatography (petroleum ether/ethyl acetate=1/1 to 1/4) to give the target product (R)-2-(4-(6-fluoroquinolin-4-yl)cyclohexyl)propanoic acid for 1h (250 mg, colorless oil) with a yield of 76%.

MS m/z (ESI): 302[M+1]

Step 8

(R)-2-((1s,4S)-4-(6-fluoroquinolin-4-yl)cyclohexyl)-N-(4-(pentafluoro-$\lambda^6$-sulfanyl)phenyl)propanamide Compound (R)-2-(4-(6-fluoroquinolin-4-yl)cyclohexyl)propanoic acid 1h (250 mg, colorless oil) was dissolved in dichloromethane (10 mL) and cooled to 0□. Oxalyl chloride (254 mg, 2 mmol) and N,N-dimethylformamide (0.025 mL) were added sequentially. After gradually warming to room temperature, the mixture was stirred for 1 hour and the solvent was removed under reduced pressure. The residue was mixed with 4-(pentafluoro-λ6-sulfanyl)aniline (328 mg, 1.5 mmol), triethylamine (202 mg, 2 mmol) and dichloromethane (20 mL) and heated to reflux for 3 hours. After cooling to room temperature, the solvent was removed under reduced pressure, and the residue was purified by reversed-phase preparative high performance liquid chromatography to give the target product (R)-2-((1s,4S)-4-(6-fluoroquinolin-4-yl)cyclohexyl)-N-(4-(pentafluoro-$\lambda^6$-sulfanyl)phenyl)propanamide 1 (97.1 mg, white solid) with a yield of 18%; and (R)-2-((1r,4R)-4-(6-fluoroquinolin-4-yl)cyclohexyl)-N-(4-(pentafluoro-$\lambda^6$-sulfanyl)phenyl)propanamide 2 (61.6 mg, white solid) with a yield of 11%.

MS m/z (ESI): 503[M+1]

$^1$H NMR (400 MHz, CD$_3$OD) δ 8.81 (d, J=4.7 Hz, 1H), 8.11 (dd, J=9.3, 5.6 Hz, 1H), 7.92 (dd, J=10.6, 2.7 Hz, 1H), 7.85-7.73 (m, 4H), 7.67-7.56 (m, 2H), 3.47 (d, J 3.5 Hz, 1H), 2.95 (dd, J=10.9, 6.8 Hz, 1H), 2.17-2.03 (m, 2H), 2.01-1.77 (m, 7H), 1.30 (d, J=6.8 Hz, 3H).
Example 2
(R)-2-((1r,4R)-4-(6-fluoroquinolin-4-yl)cyclohexyl)-N-(4-(pentafluoro-λ⁶-sulfanyl)phenyl)propanamide
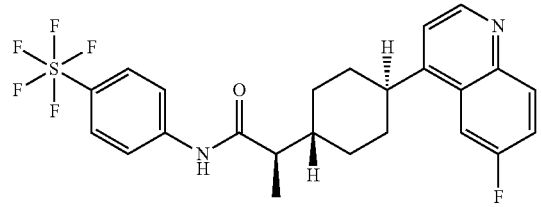
Example 2 was obtained from the synthesis of Example 1.
MS m/z (ESI): 503[M+1]
¹H NMR (400 MHz, CD₃OD) δ 9.13 (s, 1H), 8.35 (s, 2H), 8.09 (d, J=3.2 Hz, 2H), 7.81 (t, J=7.6 Hz, 4H), 3.65 (t, J=11.9 Hz, 1H), 2.45 (dd, J=14.4, 7.1 Hz, 1H), 2.20 (s, 4H), 1.88-1.73 (m, 3H), 1.64-1.43 (m, 2H), 1.31 (d, J=6.9 Hz, 3H).
Example 3
(R)-2-((1s,4S)-4-(2-methylpyridin-4-yl)cyclohexyl)-N-(4-(pentafluoro-λ⁶-sulfanyl)phenyl)propanamide
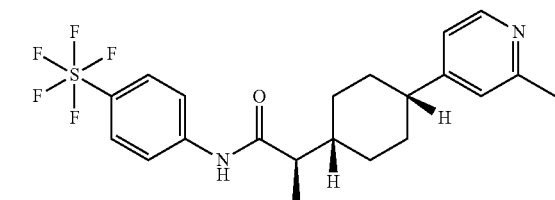
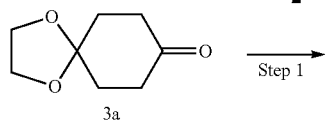
3a
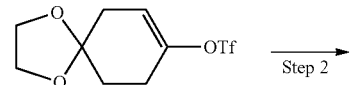
3b
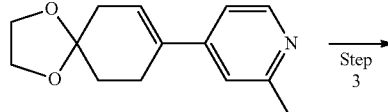
3c
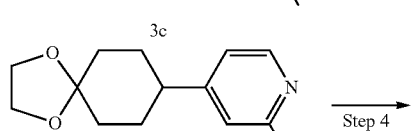
3d
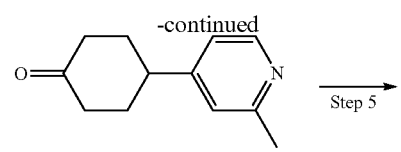
3e
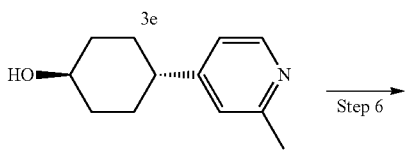
3f
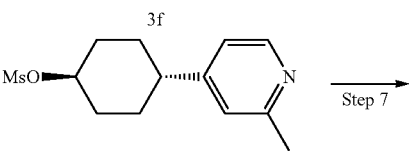
3g
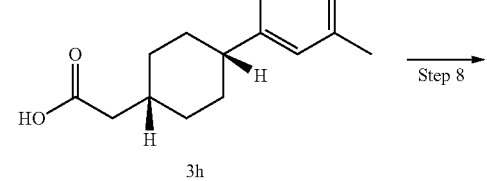
3h
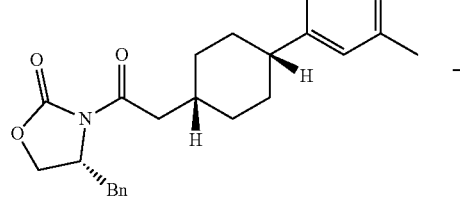
3i
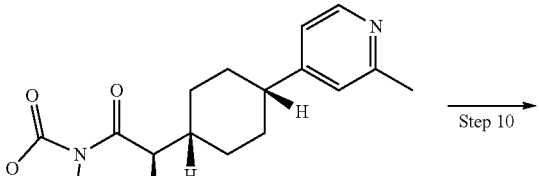
3j
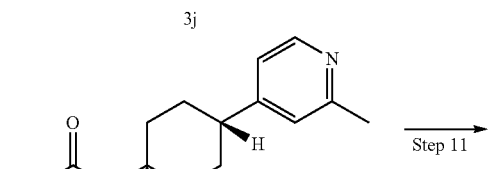
3k
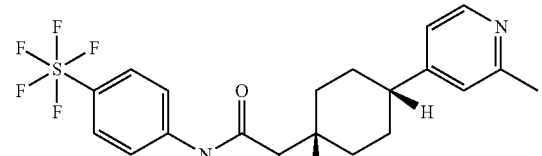
3

Step 1

1,4-Dioxaspiro[4.5]dec-7-en-8-yl trifluoromethanesulfonate

Compound 1,4-dioxaspiro[4.5]decan-8-one 3a (50 g, 320 mmol) was dissolved in anhydrous tetrahydrofuran (500 mL), cooled to −40□ under a nitrogen atmosphere, then added with a solution of sodium bis(trimethylsilyl)amide in tetrahydrofuran (2 M, 192 mL, 384 mmol). After stirring at −40° C. for 1 hour, the mixture was gradually added with a solution of N,N-bis(trifluoromethylsulfonyl)aniline (137 g, 384 mmol) in tetrahydrofuran (200 mL) and stirred for 1 hour. After the reaction was completed, it was quenched with saturated potassium bisulfate solution (50 mL). After filtration, the solvent was removed under reduced pressure. The residue was dissolved in a mixed solvent of methyl tert-butyl ether (500 mL) and petroleum ether (500 mL) then filtered. The filtrate was washed with 30% sodium hydroxide solution (200 mL×3) and dried over anhydrous sodium sulfate. The solvent was removed under reduced pressure to give the target product 1,4-dioxaspiro[4.5]dec-7-en-8-yl trifluoromethanesulfonate 3b (71.5 g, colorless oil) with a yield of 77%.

$^1$H NMR (400 MHz, CDCl$_3$) δ 5.66 (tt, J=4.0, 1.3 Hz, 1H), 4.05-3.93 (m, 4H), 2.60-2.47 (m, 2H), 2.41 (dt, J=4.0, 2.5 Hz, 2H), 1.90 (t, J=6.6 Hz, 2H).

Step 2

2-Methyl-4-(1,4-dioxaspiro[4.5]dec-7-en-8-yl)pyridine

A mixture of 1,4-dioxaspiro[4.5]dec-7-en-8-yl trifluoromethanesulfonate 3b (4.0 g, 13.9 mmol), 2-methyl-4-pyridineboronic acid (1.58 g, 11.6 mmol), [1,1'-bis(diphenylphosphino)ferrocene]palladium dichloride dichloromethane complex (422 mg, 0.57 mmol), potassium carbonate (2.39 g, 17.4 mmol), water (10 mL) and 1,4-dioxane (50 mL) was heated to 100□ under nitrogen atmosphere and stirred for 3 hours. The reaction mixture was cooled to room temperature, concentrated under reduced pressure, and the residue was purified by silica gel column chromatography (dichloromethane/methanol=9/1) to give the target product 2-methyl-4-(1,4-dioxaspiro[4.5]dec-7-en-8-yl)pyridine 3c (2.3 g, colorless oil) with a yield of 86%.

MS m/z (ESI): 232[M+1]

Step 3

2-Methyl-4-(1,4-dioxaspiro[4.5]decan-8-yl)pyridine

2-Methyl-4-(1,4-dioxaspiro[4.5]dec-7-en-8-yl)pyridine 3c (2.3 g, 9.95 mmol) was dissolved in methanol (30 mL), then added with 10% palladium on carbon (230 mg). The mixture was stirred at room temperature for 2 hours under a hydrogen atmosphere and filtered. The filtrate was concentrated under reduced pressure to give the target product 2-methyl-4-(1,4-dioxaspiro[4.5]decan-8-yl)pyridine 3d (2.3 g, colorless oil) with a yield of 99%.

MS m/z (ESI): 234[M+1]

Step 4

4-(2-Methylpyridin-4-yl)cyclohexan-1-one

Compound 2-methyl-4-(1,4-dioxaspiro[4.5]decan-8-yl)pyridine 3d (2.3 g, 9.87 mmol) was dissolved in tetrahydrofuran (30 mL), then added with 6N hydrochloric acid (5 mL). The mixture was heated to 50□ and stirred for 18 hours. The solvent was removed under reduced pressure and the residue was neutralized with saturated sodium bicarbonate solution (5 mL) then extracted with ethyl acetate (50 mL×3). After the organic phases were combined, the solvent was removed under reduced pressure, and the residue was purified by silica gel column chromatography (dichloromethane/methanol=9/1) to give the target product 4-(2-methylpyridin-4-yl)cyclohexan-1-one 3e (1.8 g, colorless oil) with a yield of 96%.

MS m/z (ESI): 190[M+1]

Step 5

(1r,4r)-4-(2-Methylpyridin-4-yl)cyclohexan-1-ol

Compound 4-(2-methylpyridin-4-yl)cyclohexan-1-one 3e (1.8 g, colorless oil) was dissolved in isopropanol (30 mL), cooled to 0□and added with sodium borohydride (361 mg, 9.52 mmol). After stirring at 0□ for 1 hour, the mixture was quenched with saturated ammonium chloride solution and filtered. The solvent in the filtrate was removed under reduced pressure, and the residue was purified by silica gel column chromatography (dichloromethane/methanol=9/1) to give the target product (1r,4r)-4-(2-methylpyridin-4-yl)cyclohexan-1-ol 3f (1.6 g, colorless oil) with a yield of 88%.

MS m/z (ESI): 192[M+1]

Step 6

(1r,4r)-4-(2-Methylpyridin-4-yl)cyclohexyl methanesulfonate

Compound (1r,4r)-4-(2-methylpyridin-4-yl)cyclohexan-1-ol 3f (1.6 g, 8.37 mmol) was dissolved in anhydrous tetrahydrofuran (30 mL) and cooled to 0□ then added with triethylamine (1.27 g, 12.6 mmol) and methanesulfonyl chloride (1.06 g, 9.21 mmol). The mixture was stirred at 0□ for 1 hour and filtered. The solvent in the filtrate was removed under reduced pressure, and the residue was purified by silica gel column chromatography (dichloromethane/methanol=9/1) to give the target product (1r,4r)-4-(2-methylpyridin-4-yl)cyclohexyl methanesulfonate 3g (2.2 g, colorless oil) with a yield of 98%.

MS m/z (ESI): 270[M+1]

Step 7

2-((1s,4s)-4-(2-Methylpyridin-4-yl)cyclohexyl)acetic acid

Di-tert-butyl malonate (5.54 g, 25.6 mmol) was dissolved in anhydrous tetrahydrofuran (30 mL), cooled to 0□, then added with 60% sodium hydride (1.02 g, 25.5 mmol). After stirring for 30 min, the mixture was added with (1r,4r)-4-(2-methylpyridin-4-yl)cyclohexyl methanesulfonate 3g (2.2 g, 8.17 mmol), heated to 90° C. and stirred for 18 hours. After cooling to room temperature, the mixture was adjusted to pH=2 with 6 N hydrochloric acid, then heated to 100° C. and stirred for 18 hours. After cooling to room temperature, the solvent was removed under reduced pressure and the residue was purified by silica gel column chromatography (dichloromethane/methanol=9/1) to give the target product 2-((1s,4s)-4-(2-methylpyridin-4-yl)cyclohexyl)acetic acid 3h (1.9 g, colorless oil) with a yield of 99%.

MS m/z (ESI): 234[M+1]

Step 8

(R)-4-Benzyl-3-(2-((1s,4S)-4-(2-methylpyridin-4-yl)cyclohexyl)acetyl)oxazolidin-2-one Compound 2-((1s,4s)-4-(2-methylpyridin-4-yl)cyclohexyl)acetic acid 3h (1.9 g, 8.14 mmol) was dissolved in anhydrous tetrahydrofuran (20 mL) then added with triethylamine (1.73 g, 17.16 mmol). The mixture was cooled to −78° C. under nitrogen atmosphere then added with pivaloyl chloride (1.13 g, 9.44 mmol) dropwise. After stirring the mixture at 0° C. for one hour, a suspension was obtained for future use.

(R)-4-Benzyloxazolidin-2-one (1.97 g, 11.15 mmol) was dissolved in anhydrous tetrahydrofuran (10 mL), cooled to −78° C., then added with a solution of n-butyllithium in hexane (2.5 M, 4.4 mL, 11 mmol) dropwise under nitrogen atmosphere. After stirring at −78° C. for 15 minutes, the mixture was gradually warmed to 0° C. and stirred for 15 minutes. The resulting pale-yellow solution was then cooled to −78° C. again for future use.

The above suspension was cooled to −78° C. then added with the pale-yellow solution cooled to −78° C. The reaction mixture was gradually warmed to room temperature and stirred for 3 hours. The reaction mixture was added with saturated ammonium chloride solution (100 mL) and extracted with ethyl acetate (100 mL×3). The organic phases were combined, washed with saturated brine (20 mL×2), dried over anhydrous sodium sulfate, and filtered. The solvent in the filtrate was removed under reduced pressure and the residue was purified by silica gel column chromatography (dichloromethane/methanol=9/1) to give the target product (R)-4-benzyl-3-(2-((1s,4S)-4-(2-methylpyridin-4-yl)cyclohexyl)acetyl)oxazolidin-2-one 3i (3.02 g, colorless oil) with a yield of 91%.

MS m/z (ESI): 393[M+1]

Step 9

(R)-4-Benzyl-3-((R)-2-((1s,4S)-4-(2-methylpyridin-4-yl)cyclohexyl)propanoyl)oxazolidin-2-one (R)-4-Benzyl-3-(2-((1s,4S)-4-(2-methylpyridin-4-yl)cyclohexyl)acetyl)oxazolidin-2-one 3i (3 g, 7.65 mmol) was dissolved in anhydrous tetrahydrofuran (30 mL), cooled to −50° C., then added with a solution of sodium bis(trimethylsilyl)amide in tetrahydrofuran (2 M, 7.7 mL, 15.4 mmol). After stirring for 30 min, the mixture was added with methyl iodide (1.63 g, 11.48 mmol) and stirred for another 3 hours. After quenching with saturated ammonium chloride solution (10 mL), the mixture was gradually warmed to room temperature and extracted with ethyl acetate (50 mL×3). The organic phases were combined, washed with saturated brine (20 mL), dried over anhydrous sodium sulfate, and filtered. The solvent in the filtrate was removed under reduced pressure and the residue was purified by silica gel column chromatography (dichloromethane/methanol=9/1) to give the target product (R)-4-benzyl-3-((R)-2-((1s,4S)-4-(2-methylpyridin-4-yl)cyclohexyl)propanoyl)oxazolidin-2-one 3j (3.02 g, colorless oil) with a yield of 96%.

MS m/z (ESI): 407[M+1]

Step 10

(R)-2-((1s,4S)-4-(2-methylpyridin-4-yl)cyclohexyl)propanoic acid (R)-4-benzyl-3-((R)-2-((1s,4S)-4-(2-methylpyridin-4-yl)cyclohexyl)propanoyl)oxazolidin-2-one 3j (3 g, 7.38 mmol), water (10 mL) and tetrahydrofuran (30 mL) were mixed, cooled to 0° C., then added with 35% hydrogen peroxide solution (2 mL) and lithium hydroxide monohydrate (266 mg, 11.03 mmol). After gradually warming to room temperature, the mixture was stirred for 1 hour. After re-cooling to 0° C., the reaction mixture was quenched with saturated sodium sulfite solution. The mixture was extracted with ethyl acetate (50 mL×3). After the organic phases were combined, the solvent was removed under reduced pressure and the residue was purified by silica gel column chromatography (dichloromethane/methanol=9/1), and further purified by reversed-phase high-performance liquid chromatography to give the target product (R)-2-((1s,4S)-4-(2-methylpyridin-4-yl)cyclohexyl)propanoic acid 3k (500 mg, colorless oil) with a yield of 27%.

MS m/z (ESI): 248[M+1]

Step 11

(R)-2-((1s,4S)-4-(2-methylpyridin-4-yl)cyclohexyl)-N-(4-(pentafluoro-$\lambda^6$-sulfanyl)phenyl)propanamide Compound (R)-2-((1s,4S)-4-(2-methylpyridin-4-yl)cyclohexyl)propanoic acid 3k (50 mg, 0.202 mmol) was dissolved in dichloromethane (10 mL), then added with oxalyl chloride (0.5 mL). After stirring at room temperature for 30 min, the solvent was removed under reduced pressure and the residue was dissolved in tetrahydrofuran (10 mL) with 4-(pentafluoro-$\lambda^6$-sulfanyl)aniline (44 mg, 0.2 mmol) and triethylamine (41 mg, 0.4 mmol). After stirring at room temperature for 3 hours, the solvent was removed under reduced pressure, and the residue was purified by reversed-phase high-performance liquid chromatography to give the target product (R)-2-((1s,4S)-4-(2-methylpyridin-4-yl)cyclohexyl)-N-(4-(pentafluoro-X-sulfanyl)phenyl)propanamide 3 (27 mg, white solid) with a yield of 30%.

MS m/z (ESI): 449[M+1]

$^1$H NMR (400 MHz, CD$_3$OD) δ 8.32 (d, J=5.1 Hz, 1H), 7.78 (brs, 4H), 7.35-7.19 (m, 2H), 2.75 (d, J=6.6 Hz, 2H), 2.54 (s, 3H), 2.02-1.99 (m, 2H), 1.87-1.61 (m, 7H), 1.24 (d, J=6.6 Hz, 3H).

Example 4

(R)—N-(4-(pentafluoro-$\lambda^6$-sulfanyl)phenyl)-2-(4-(pyrazolo[1,5-a]pyrimidin-7-yl)cyclohexyl)propanamide

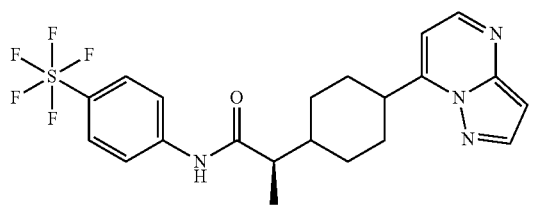

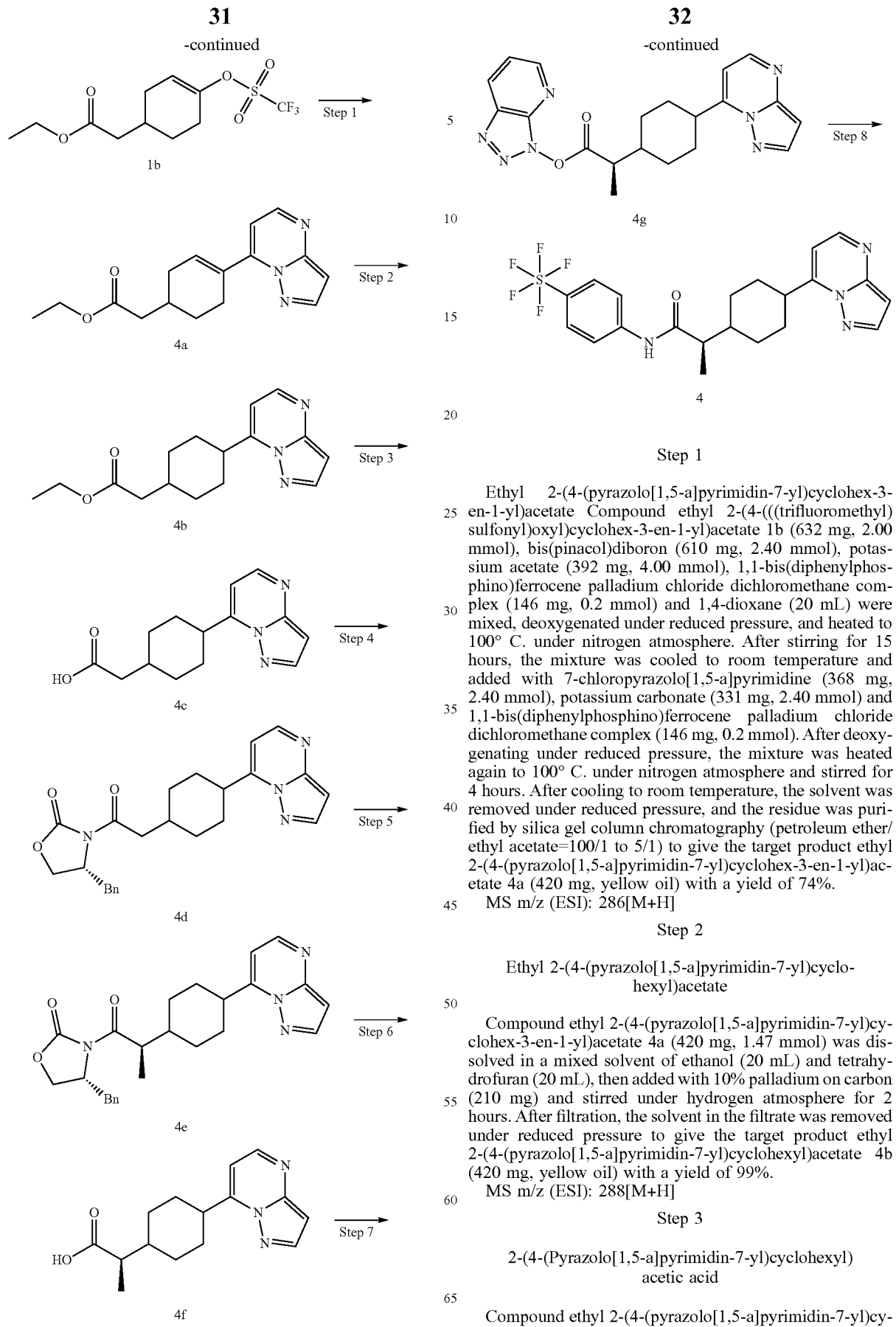

Step 1

Ethyl 2-(4-(pyrazolo[1,5-a]pyrimidin-7-yl)cyclohex-3-en-1-yl)acetate Compound ethyl 2-(4-(((trifluoromethyl)sulfonyl)oxyl)cyclohex-3-en-1-yl)acetate 1b (632 mg, 2.00 mmol), bis(pinacol)diboron (610 mg, 2.40 mmol), potassium acetate (392 mg, 4.00 mmol), 1,1-bis(diphenylphosphino)ferrocene palladium chloride dichloromethane complex (146 mg, 0.2 mmol) and 1,4-dioxane (20 mL) were mixed, deoxygenated under reduced pressure, and heated to 100° C. under nitrogen atmosphere. After stirring for 15 hours, the mixture was cooled to room temperature and added with 7-chloropyrazolo[1,5-a]pyrimidine (368 mg, 2.40 mmol), potassium carbonate (331 mg, 2.40 mmol) and 1,1-bis(diphenylphosphino)ferrocene palladium chloride dichloromethane complex (146 mg, 0.2 mmol). After deoxygenating under reduced pressure, the mixture was heated again to 100° C. under nitrogen atmosphere and stirred for 4 hours. After cooling to room temperature, the solvent was removed under reduced pressure, and the residue was purified by silica gel column chromatography (petroleum ether/ethyl acetate=100/1 to 5/1) to give the target product ethyl 2-(4-(pyrazolo[1,5-a]pyrimidin-7-yl)cyclohex-3-en-1-yl)acetate 4a (420 mg, yellow oil) with a yield of 74%.

MS m/z (ESI): 286[M+H]

Step 2

Ethyl 2-(4-(pyrazolo[1,5-a]pyrimidin-7-yl)cyclohexyl)acetate

Compound ethyl 2-(4-(pyrazolo[1,5-a]pyrimidin-7-yl)cyclohex-3-en-1-yl)acetate 4a (420 mg, 1.47 mmol) was dissolved in a mixed solvent of ethanol (20 mL) and tetrahydrofuran (20 mL), then added with 10% palladium on carbon (210 mg) and stirred under hydrogen atmosphere for 2 hours. After filtration, the solvent in the filtrate was removed under reduced pressure to give the target product ethyl 2-(4-(pyrazolo[1,5-a]pyrimidin-7-yl)cyclohexyl)acetate 4b (420 mg, yellow oil) with a yield of 99%.

MS m/z (ESI): 288[M+H]

Step 3

2-(4-(Pyrazolo[1,5-a]pyrimidin-7-yl)cyclohexyl)acetic acid

Compound ethyl 2-(4-(pyrazolo[1,5-a]pyrimidin-7-yl)cyclohexyl)acetate 4b (420 mg, 1.46 mmol) was dissolved in tetrahydrofuran (20 mL) then added with lithium hydroxide aqueous solution (1 M, 3 mL, 3 mmol). After stirring at room temperature for 24 hours, the mixture was adjusted to pH 6-7 with 1 N hydrochloric acid and the solvent was removed under reduced pressure. The residue was purified by reversed-phase preparative high performance liquid chromatography to give the target product 2-(4-(pyrazolo[1,5-a]pyrimidin-7-yl)cyclohexyl)acetic acid 4c (300 mg, white solid) with a yield of 79%.

MS m/z (ESI): 260[M+H]

Step 4

(R)-4-Benzyl-3-(2-(4-(pyrazolo[1,5-a]pyrimidin-7-yl)cyclohexyl)acetyl)oxazolidin-2-one 2-(4-(Pyrazolo[1,5-a]pyrimidin-7-yl)cyclohexyl)acetic acid 4c (300 mg, 1.16 mmol) and triethylamine (236 mg, 2.32 mmol) were dissolved in tetrahydrofuran (20 mL), cooled to −10° C., and then added with pivaloyl chloride (174 mg, 1.45 mmol). After gradually warming to room temperature and stirring for 30 min, the mixture was cooled to −78° C. for future use.

(R)-4-benzyloxazolidin-2-one (268 mg, 1.51 mmol) was dissolved in anhydrous tetrahydrofuran (20 mL), cooled to −78° C., and then added with n-butyllithium (2.4 M, 0.63 mL, 1.51 mmol) and stirred at this temperature for 30 min to give a clear solution. This solution was gradually added dropwise to the aforementioned mixture cooled at −78° C., and then gradually warmed to room temperature while stirring. The resulting mixture was stirred for 30 min. The solvent was removed under reduced pressure, and the residue was purified by reversed-phase preparative high performance liquid chromatography to give the target product (R)-4-benzyl-3-(2-(4-(pyrazolo[1,5-a]pyrimidin-7-yl)cyclohexyl)acetyl)oxazolidin-2-one 4d (410 mg, white solid) with a yield of 84%.

MS m/z (ESI): 419[M+H]

Step 5

(R)-4-Benzyl-3-((R)-2-(4-(pyrazolo[1,5-a]pyrimidin-7-yl)cyclohexyl)propanoyl)oxazolidin-2-one (R)-4-benzyl-3-(2-(4-(pyrazolo[1,5-a]pyrimidin-7-yl)cyclohexyl)acetyl)oxazolidin-2-one 4d (410 mg, 0.98 mmol) was dissolved in anhydrous tetrahydrofuran (20 mL), cooled to −50° C., and then added with a solution of sodium bis(trimethylsilyl)amide in tetrahydrofuran (2 N, 0.98 mL, 1.96 mmol). The mixture was stirred for 1 hour then added with iodomethane (417 mg, 2.94 mmol) dropwise and stirred at −50° C. for another 5 hours. Saturated citric acid solution (2 mL) was added to the reaction mixture and the temperature was raised to room temperature, then saturated brine (10 mL) was added and the resulting mixture was extracted with ethyl acetate (50 mL×2). The organic phases were combined and dried over anhydrous sodium sulfate. After filtration, the solvent in the filtrate was removed under reduced pressure. The residue was purified by reversed-phase preparative high performance liquid chromatography to give the target product (R)-4-benzyl-3-((R)-2-(4-(pyrazolo[1,5-a]pyrimidin-7-yl)cyclohexyl)propanoyl)oxazolidin-2-one 4e (300 mg, white solid) with a yield of 71%.

MS m/z (ESI): 433[M+H]

Step 6

(R)-2-(4-(Pyrazolo[1,5-a]pyrimidin-7-yl)cyclohexyl)propanoic acid (R)-4-benzyl-3-((R)-2-(4-(pyrazolo[1,5-a]pyrimidin-7-yl)cyclohexyl)propanoyl)oxazolidin-2-one 4e (300 mg, 0.69 mmol), 30% hydrogen peroxide solution (0.5 mL) and tetrahydrofuran (15 mL) were mixed, cooled to 0° C., then added with lithium hydroxide aqueous solution (1 N, 1 mL) and gradually warmed to room temperature. After stirring for 15 hours, formic acid (0.5 mL) was added, and the solvent was removed under reduced pressure. The residue was purified by reversed-phase preparative high performance liquid chromatography to give the target product (R)-2-(4-(pyrazolo[1,5-a]pyrimidin-7-yl)cyclohexyl)propanoic acid 4f (130 mg, white solid) with a yield of 69%.

MS m/z (ESI): 274[M+H]

Step 7

3H-[1,2,3]triazolo[4,5-b]pyridin-3-yl (R)-2-(4-(pyrazolo[1,5-a]pyrimidin-7-yl)cyclohexyl)propanoate (R)-2-(4-(pyrazolo[1,5-a]pyrimidin-7-yl)cyclohexyl)propanoic acid 4f (40 mg, 0.146 mmol) and triethylamine (45 mg, 0.44 mmol) were dissolved in N,N-dimethylformamide (2 mL), then added with 2-(7-aza-H-benzotriazole-1-yl)-1,1,3,3-tetramethyluronium hexafluorophosphate (167 mg, 0.44 mmol) and stirred for 1 hour. The solvent was removed under reduced pressure, and the residue was purified by reversed-phase preparative high performance liquid chromatography to give the target product 3H-[1,2,3]triazolo[4,5-b]pyridin-3-yl (R)-2-(4-(pyrazolo[1,5-a]pyrimidin-7-yl)cyclohexyl)propanoate 4g (40 mg, white solid) with a yield of 70%.

MS m/z (ESI): 392[M+H]

Step 8

(R)—N-(4-(pentafluoro-$\lambda^6$-sulfanyl)phenyl)-2-(4-(pyrazolo[1,5-a]pyrimidin-7-yl)cyclohexyl)propanamide Compound 4-(pentafluoro-λ6-sulfanyl)aniline (45 mg, 0.2 mmol) was dissolved in tetrahydrofuran (3 mL), cooled to 0° C., then added with sodium hydride (60%, 6 mg, 0.15 mmol). After stirring for 30 min, 3H-[1,2,3]triazolo[4,5-b]pyridin-3-yl (R)-2-(4-(pyrazolo[1,5-a]pyrimidin-7-yl)cyclohexyl)propanoate 4g (40 mg, 0.1 mmol) in tetrahydrofuran (1 mL) was added. After stirring at room temperature for 1 hour, the reaction mixture was quenched with water (0.5 mL), and the solvent was removed under reduced pressure. The residue was purified by reversed-phase preparative high performance liquid chromatography to give the target product (R)—N-(4-(pentafluoro-$\lambda^6$-sulfanyl)phenyl)-2-(4-(pyrazolo[1,5-a]pyrimidin-7-yl)cyclohexyl)propanamide 4 (1.1 mg, white solid) with a yield of 2%.

MS m/z (ESI): 475[M+1]

$^1$H NMR (400 MHz, CD$_3$OD) δ 8.36 (dd, J=11.6, 4.4 Hz, 1H), 8.07 (t, J=2.1 Hz, 1H), 7.77-7.53 (m, 4H), 6.84 (dd, J=34.1, 4.4 Hz, 1H), 6.62-6.54 (m, 1H), 3.59 (s, 1H), 2.72 (dd, J=10.7, 6.8 Hz, 1H), 2.30-2.15 (m, 1H), 2.08 (dd, J=27.4, 13.8 Hz, 1H), 1.97-1.89 (m, 2H), 1.85 (s, 1H), 1.77-1.58 (m, 3H), 1.56-1.45 (m, 1H), 1.15 (dd, J=6.8, 2.8 Hz, 3H).

Example 5

2-(4-(6-fluoroquinolin-4-yl)-1-hydroxycyclohexyl)-N-(4-(pentafluoro-λ⁶-sulfanyl)phenyl)acetamide

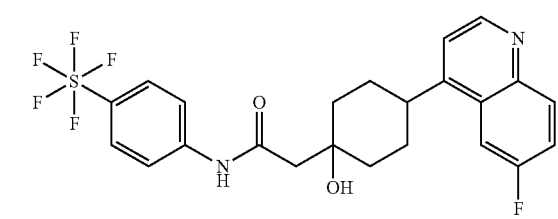

5

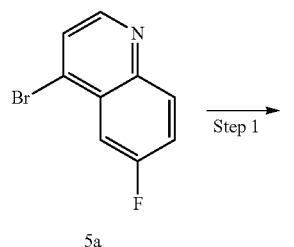

5a

Step 1

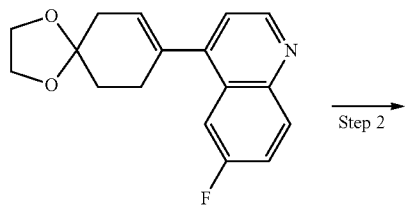

5b

Step 2

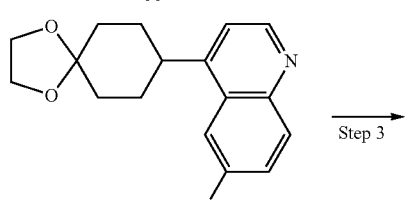

5c

Step 3

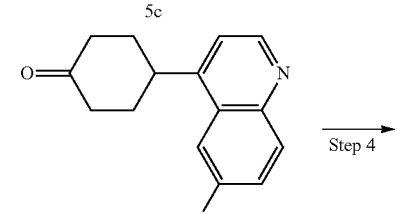

5d

Step 4

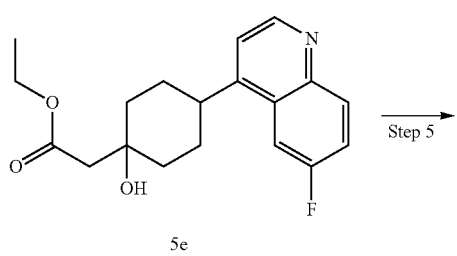

5e

Step 5

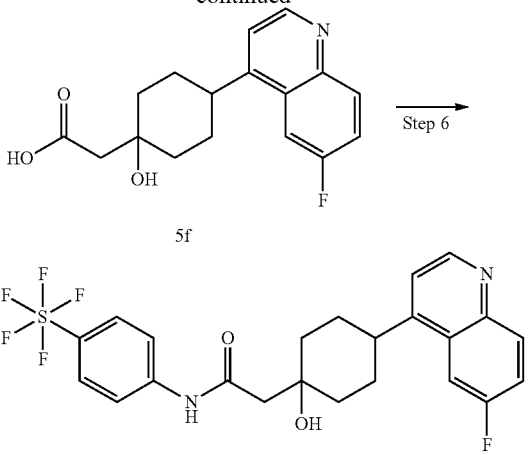

5f

Step 6

5

Step 1

6-Fluoro-4-(1,4-dioxaspiro[4.5]dec-7-en-8-yl)quinoline

4-Bromo-6-fluoroquinoline 5a (5 g, 22.12 mmol), 4,4,5,5-tetramethyl-2-(1,4-dioxaspiro[4.5]dec-7-en-8-yl)-1,3,2-dioxaborolane (6.5 g, 24.3 mmol), potassium carbonate (6.1 g, 44.24 mmol), 1,1-bis(diphenylphosphino)ferrocene palladium chloride dichloromethane complex (0.9 g, 1.1 mmol), 1,4-dioxane (50 mL) and water (10 mL) were mixed at room temperature and heated to 100° C. under nitrogen atmosphere. The mixture was then stirred for 2 hours. After cooling to room temperature, the solvent was removed under reduced pressure, and the residue was purified by silica gel column chromatography (petroleum ether/ethyl acetate=3/1) to give the target product 6-fluoro-4-(1,4-dioxaspiro[4.5]dec-7-en-8-yl)quinoline 5b (5.2 g, light yellow solid) with a yield of 82%.

MS m/z (ESI): 286[M+1]

Step 2

6-Fluoro-4-(1,4-dioxaspiro[4.5]decan-8-yl)quinoline

6-Fluoro-4-(1,4-dioxaspiro[4.5]dec-7-en-8-yl)quinoline 5b (5 g, 17.54 mmol), 10% palladium on carbon (500 mg) and ethanol (50 mL) were mixed, then stirred at room temperature for 5 hours under hydrogen atmosphere. After the reaction was completed, the mixture was filtered and the solvent was removed from the filtrate under reduced pressure to give the target product 6-fluoro-4-(1,4-dioxaspiro[4.5]decan-8-yl)quinoline 5c (4.5 g, colorless oil) with a yield of 90%.

MS m/z (ESI): 288[M+1]

Step 3

4-(6-Fluoroquinolin-4-yl)cyclohexan-1-one

6-Fluoro-4-(1,4-dioxaspiro[4.5]decan-8-yl)quinoline 5c (4.5 g, 15.68 mmol) was dissolved in acetone (50 mL), then added with concentrated hydrochloric acid (1 mL) and stirred at room temperature overnight. After the reaction was completed, the solvent was removed under reduced pressure, and the residue was extracted with ethyl acetate (100 mL×2). The organic phases were combined, washed with saturated brine and dried over anhydrous sodium sulfate. After filtering, the solvent was removed under reduced pressure to give the target product 4-(6-fluoroquinolin-4-yl)cyclohexan-1-one 5d (3.6 g, colorless oil) with a yield of 94%.

MS m/z (ESI): 244[M+1]

Step 4

Ethyl 2-(4-(6-fluoroquinolin-4-yl)-1-hydroxycyclohexyl)acetate

Ethyl acetate (440 mg, 4.92 mmol) was dissolved in anhydrous tetrahydrofuran (10 mL), cooled to −78° C., then added with a solution of lithium bis(trimethylsilyl)amide in tetrahydrofuran (1 M, 5.7 mL, 5.7 mmol). After stirring for 1 hour, a solution of 4-(6-fluoroquinolin-4-yl)cyclohexane-1-one 5d (1 g, 4.1 mmol) in tetrahydrofuran (4 mL) was added dropwise. The reaction was gradually warmed to room temperature and stirred for 1 hour. After quenching with hydrochloric acid (1 N, 10 mL), water (100 mL) was added and the mixture was extracted with ethyl acetate (100 mL×3). The organic phases were combined, washed with saturated brine (100 mL) and dried over anhydrous sodium sulfate. After filtration, the solvent was removed from the filtrate under reduced pressure, and the residue was purified by silica gel column chromatography (petroleum ether/ethyl acetate=100/0 to 2/3) to give the target product ethyl 2-(4-(6-fluoroquinolin-4-yl)-1-hydroxycyclohexyl)acetate 5e (1.2 g, colorless oil) with a yield of 83%.

MS m/z (ESI): 332[M+H]

Step 5

2-(4-(6-Fluoroquinolin-4-yl)-1-hydroxycyclohexyl)acetic acid

To a mixture of ethyl 2-(4-(6-fluoroquinolin-4-yl)-1-hydroxycyclohexyl)acetate 5e (600 mg, 1.81 mmol), water (1 mL) and tetrahydrofuran (6 mL) was added lithium hydroxide monohydrate (114 mg, 2.71 mmol). After stirring at room temperature for 1 hour, the solvent was removed under reduced pressure, and the residue was purified by silica gel column chromatography (petroleum ether/ethyl acetate=100/0 to 1/9) to give the target product 2-(4-(6-fluoroquinolin-4-yl)-1-hydroxycyclohexyl)acetic acid 5f (230 mg, white solid) with a yield of 41%.

MS m/z (ESI): 304[M+H]

Step 6

2-(4-(6-fluoroquinolin-4-yl)-1-hydroxycyclohexyl)-N-(4-(pentafluoro-λ$^6$-sulfanyl)phenyl)acetamide 2-(4-(6-Fluoroquinolin-4-yl)-1-hydroxycyclohexyl)acetic acid 5f (150 mg, 0.5 mmol), 4-(pentafluoro-λ$^6$-sulfanyl) aniline (330 mg, 1.5 mmol), 2-(7-aza-1H-benzotriazole-1-yl)-1,1,3,3-tetramethyluronium hexafluorophosphate (250 mg, 0.65 mmol), diisopropylethylamine (260 mg, 2.0 mmol) and N,N-dimethylformamide (3 mL) were mixed and stirred at room temperature for 12 hours. The reaction solution was purified by reversed-phase high performance liquid chromatography to give the target product 2-(4-(6-fluoroquinolin-4-yl)-1-hydroxycyclohexyl)-N-(4-(pentafluoro-λ$^6$-sulfanyl) phenyl)acetamide 5 (1.16 mg, white solid) with a yield of 0.5%.

MS m/z (ESI): 505[M+H]

$^1$H NMR (400 MHz, DMSO-d$_6$) δ 10.32 (s, 1H), 8.83 (d, J=4.5 Hz, 2H), 8.09 (dd, J 9.2, 5.8 Hz, 1H), 8.01 (dd, J=10.9, 2.6 Hz, 1H), 7.85 (d, J=9.7 Hz, 2H), 7.71-7.62 (m, 1H), 7.56 (d, J=4.5 Hz, 1H), 6.50 (s, 1H), 4.88 (s, 2H), 2.73 (s, 2H), 2.05-1.65 (m, 8H).

Example 6

2-(4-(6-Fluoroquinolin-4-yl)piperazin-1-yl)-N-(4-(pentafluoro-λ$^6$-sulfanyl)phenyl)propanamide

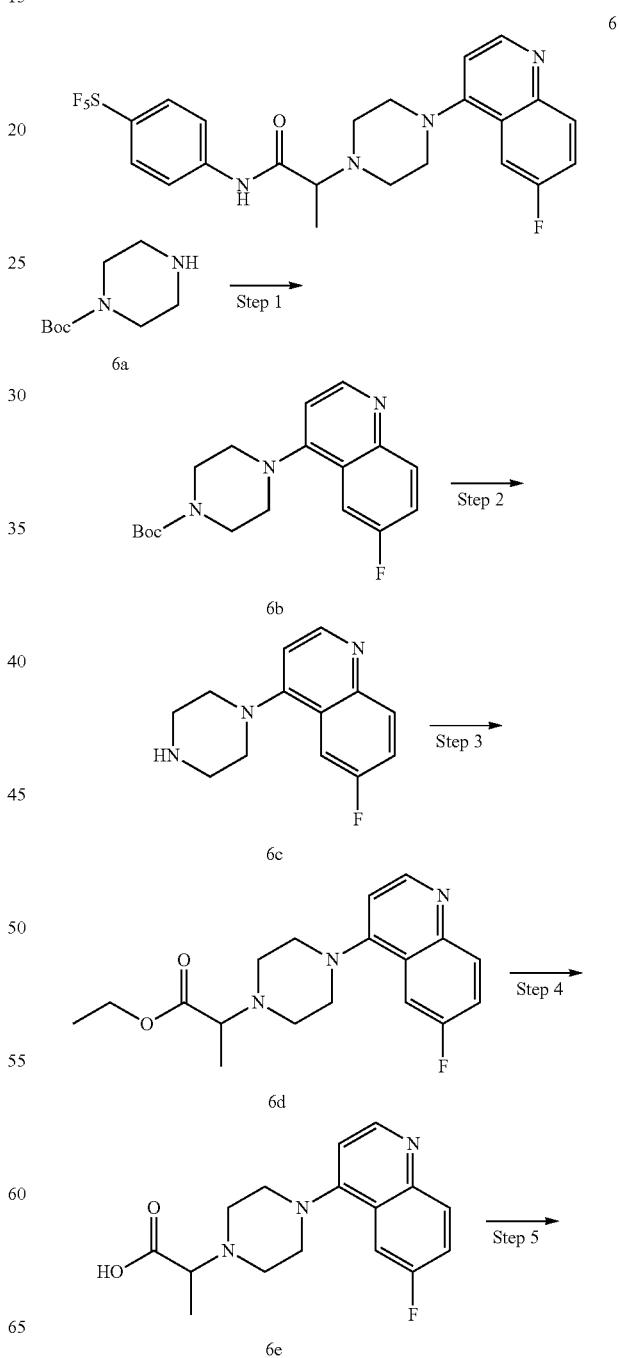

-continued

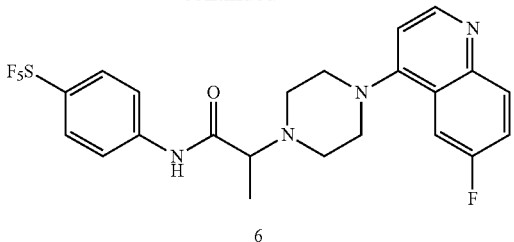

6

Step 1

Tert-butyl 4-(6-fluoroquinolin-4-yl)piperazine-1-carboxylate

Tert-butyl piperazine-1-carboxylate 6a (100 mg, 0.537 mmol), 4-bromo-6-fluoroquinoline (146 mg, 0.644 mmol), tris(dibenzylideneacetone)dipalladium (49 mg, 0.537 mmol), 4,5-bis(diphenylphosphino)-9,9-dimethylxanthene (62 mg, 0.107 mmol), cesium carbonate (350 mg, 1.074 mmol) and 1,4-dioxane (10 mL) were mixed and then heated in a microwave reactor for 30 min under a nitrogen atmosphere. After the reaction was completed, the filtrate was filtered, and the solvent was removed under reduced pressure to give the target product tert-butyl 4-(6-fluoroquinolin-4-yl)piperazine-1-carboxylate 6b (80 mg, crude product) with a yield of 45%. The crude product was used directly in the next reaction without further purification.

MS m/z (ESI): 332[M+H]

Step 2

6-Fluoro-4-(piperazin-1-yl)quinoline

The compound tert-butyl 4-(6-fluoroquinolin-4-yl)piperazine-1-carboxylate 6b (800 mg, crude product) was dissolved in a solution of hydrogen chloride in 1,4-dioxane (0.4 M, 20 mL) then stirred at room temperature for 12 hours. After the reaction was completed, the solvent was removed under reduced pressure to give the target product 6-fluoro-4-(piperazin-1-yl)quinoline 6c (800 mg, crude product). The crude product was used directly in the next reaction without further purification.

MS m/z (ESI): 232[M+H]

Step 3

Ethyl 2-(4-(6-fluoroquinolin-4-yl)piperazin-1-yl)propanoate

6-Fluoro-4-(piperazin-1-yl)quinoline 6c (800 mg, crude), ethyl 2-bromopropionate (751 mg, 4.15 mmol), triethylamine (699 mg, 6.92 mmol) and dichloromethane (10 mL) were mixed and stirred at room temperature for 12 hours. The solvent was removed under reduced pressure, and the residue was purified by silica gel column chromatography (dichloromethane/methanol=5/1) to give the target product ethyl 2-(4-(6-fluoroquinolin-4-yl)piperazin-1-yl)propanoate 6d (200 mg, 0.604 mmol) with a yield of 25% over two steps.

MS m/z (ESI): 332[M+H]

Step 4

2-(4-(6-Fluoroquinolin-4-yl)piperazin-1-yl)propanoic acid

The compound ethyl 2-(4-(6-fluoroquinolin-4-yl)piperazin-1-yl)propanoate 6d (200 mg, 0.604 mmol) was dissolved in tetrahydrofuran (10 mL), then added with lithium hydroxide monohydrate (1 g, 23 mmol) in water (5 mL) and stirred at room temperature for 12 hours. After the reaction was completed, the mixture was filtered, and the solvent was removed from the filtrate under reduced pressure. The residue was purified by reversed-phase high-performance liquid chromatography to give the target product 2-(4-(6-fluoroquinolin-4-yl)piperazin-1-yl)propanoic acid 6e (50 mg, white solid) with a yield of 27%.

MS m/z (ESI): 304[M+H]

Step 5

2-(4-(6-Fluoroquinolin-4-yl)piperazin-1-yl)-N-(4-(pentafluoro-$\lambda^6$-sulfanyl)phenyl)propanamide 2-(4-(6-Fluoroquinolin-4-yl)piperazin-1-yl)propanoic acid 6e (50 mg, 0.165 mmol), 4-(pentafluoro-$\lambda^6$-sulfanyl) aniline (144 mg, 0.66 mmol) and dichloromethane (10 mL) were mixed then added with 1-ethyl-3-(3-dimethylaminopropyl)carbodiimide hydrochloride (127 mg, 0.66 mmol). After stirring at room temperature for 3 hours, the solvent was removed under reduced pressure, and the residue was purified by reversed-phase high performance liquid chromatography to give the target product 2-(4-(6-Fluoroquinolin-4-yl)piperazin-1-yl)-N-(4-(pentafluoro-$\lambda^6$-sulfanyl)phenyl) propanamide hydrochloride 6 (15.8 mg, white solid) with a yield of 18%.

MS m/z (ESI): 505[M+H]

$^1$H NMR (400 MHz, CD$_3$OD) δ 8.69 (d, J=5.8 Hz, 1H), 8.07 (dd, J=9.2, 4.6 Hz, 1H), 7.91 (d, J=8.6 Hz, 1H), 7.81 (dd, J=17.6, 8.5 Hz, 3H), 7.72 (d, J=9.2 Hz, 2H), 7.37 (d, J=5.9 Hz, 1H), 4.33 (d, J=6.6 Hz, 1H), 4.06 (s, 4H), 3.75 (d, J=20.8 Hz, 4H), 1.71 (d, J=6.4 Hz, 3H).

Example 7

2-(1-(6-fluoroquinolin-4-yl)piperidin-4-yl)-N-(4-(pentafluoro-$\lambda^6$-sulfanyl)phenyl)propanamide

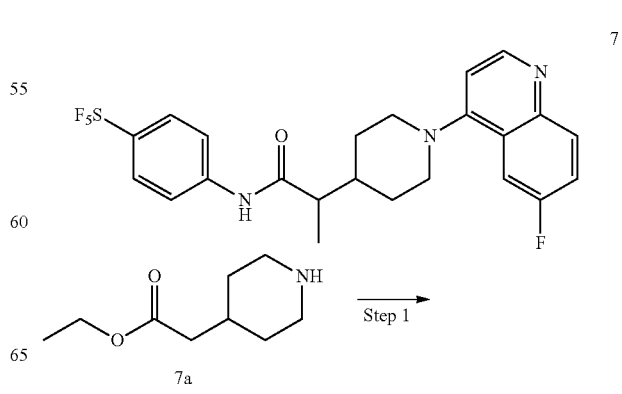

-continued

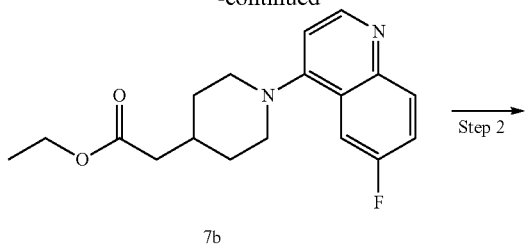

7b

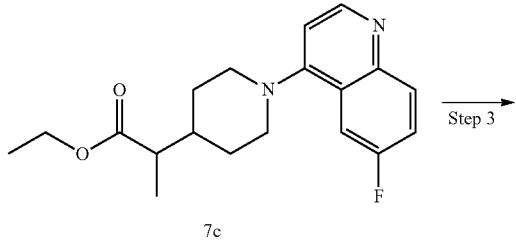

7c

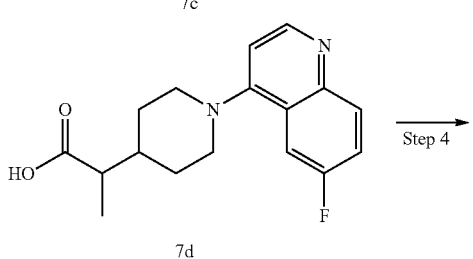

7d

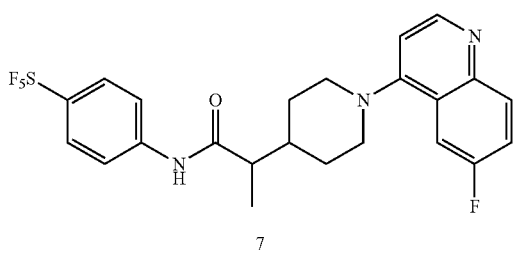

7

Step 1

Ethyl 2-(1-(6-fluoroquinolin-4-yl)piperidin-4-yl)acetate

Ethyl 2-(piperidin-4-yl)acetate 7a (500 mg, 2.92 mmol), 4-bromo-6-fluoroquinoline (791.2 mg, 3.5 mmol), tris(dibenzylideneacetone)dipalladium (267.5 mg, 0.292 mmol), 4,5-bis(diphenylphosphino)-9,9-dimethylxanthene (338 mg, 0.584 mmol), cesium carbonate (1.89 g, 5.89 mmol) and 1,4-dioxane (10 mL) were mixed, then heated in a microwave reactor for 30 min under a nitrogen atmosphere. After the reaction was completed, the mixture was filtered, and the solvent was removed under reduced pressure. The residue was purified by silica gel column chromatography (petroleum ether/ethyl acetate=1/9) to give the target product ethyl 2-(1-(6-fluoroquinolin-4-yl)piperidin-4-yl)acetate 7b (500 mg, yellow solid) with a yield of 54%.

MS m/z (ESI): 317[M+H]

Step 2

Ethyl 2-(1-(6-fluoroquinolin-4-yl)piperidin-4-yl)propanoate

Ethyl 2-(1-(6-fluoroquinolin-4-yl)piperidin-4-yl)acetate 7b (500 mg, 1.58 mmol) was dissolved in tetrahydrofuran (20 mL), cool to −40° C., then added with a solution of sodium bis(trimethylsilyl)amide in tetrahydrofuran (2 M, 0.8 mL, 1.6 mmol) dropwise. After stirring for 1 hour, the mixture was added with methyl iodide (247 mg, 1.74 mmol) and stirred for 1 hour. The reaction mixture was quenched with water and extracted with dichloromethane (50 mL×2). After the organic phases were combined, the solvent was removed under reduced pressure to give the target product ethyl 2-(1-(6-fluoroquinolin-4-yl)piperidin-4-yl)propanoate 7c (500 mg, crude). The product was used directly in the next reaction without further purification.

MS m/z (ESI): 331[M+H]

Step 3

2-(1-(6-Fluoroquinolin-4-yl)piperidin-4-yl)propanoic acid

Compound 2-(1-(6-fluoroquinolin-4-yl)piperidin-4-yl)propionic acid ethyl ester 7c (500 mg, crude product) was dissolved in tetrahydrofuran (10 mL), then added with lithium hydroxide monohydrate (1.2 g, 28.5 mmol) in water (5 mL) and stirred at room temperature for 12 hours. After the reaction was completed, the mixture was filtered, and the solvent was removed under reduced pressure. The residue was purified by reversed-phase high performance liquid chromatography to give the target product 2-(1-(6-fluoroquinolin-4-yl)piperidin-4-yl)propanoic acid 7d (137 mg, white solid).

MS m/z (ESI): 303[M+H]

Step 4

2-(1-(6-Fluoroquinolin-4-yl)piperidin-4-yl)-N-(4-(pentafluoro-λ$^{6}$-sulfanyl)phenyl)propanamide 2-(1-(6-Fluoroquinolin-4-yl)piperidin-4-yl)propanoic acid 7d (20 mg, 0.066 mmol), 4-(pentafluoro-λ$^{6}$-sulfanyl)aniline (144 mg, 0.66 mmol) and dichloromethane (10 mL) were mixed, then added with 1-ethyl-(3-dimethylaminopropyl)carbodiimide hydrochloride (100 mg, 0.5 mmol). After stirring at room temperature for 3 hours, the solvent was removed under reduced pressure, and the residue was purified by reversed-phase high performance liquid chromatography to give the target product 2-(1-(6-fluoroquinolin-4-yl)piperidin-4-yl)-N-(4-(pentafluoro-λ$^{6}$-sulfanyl)phenyl)propanamide 6 (7.28 mg, white solid) with a yield of 21%.

MS m/z (ESI): 504[M+H]

$^{1}$H NMR (400 MHz, DMSO-d6) δ 10.37 (s, 1H), 8.66 (d, J=4.9 Hz, 1H), 8.01 (dd, J 9.0, 5.7 Hz, 1H), 7.89-7.78 (m, 3H), 7.65-7.53 (m, 2H), 7.02 (d, J=5.0 Hz, 1H), 3.60-3.44 (m, 2H), 2.87-2.69 (m, 2H), 2.47-2.38 (m, 1H).

Example 8

(R)-2-((1s,4S)-4-(6-fluoroquinolin-4-yl)cyclohexyl)-N-(3-(pentafluoro-λ$^{6}$-sulfanyl)phenyl)propanamide

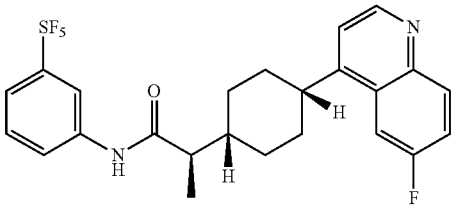

8

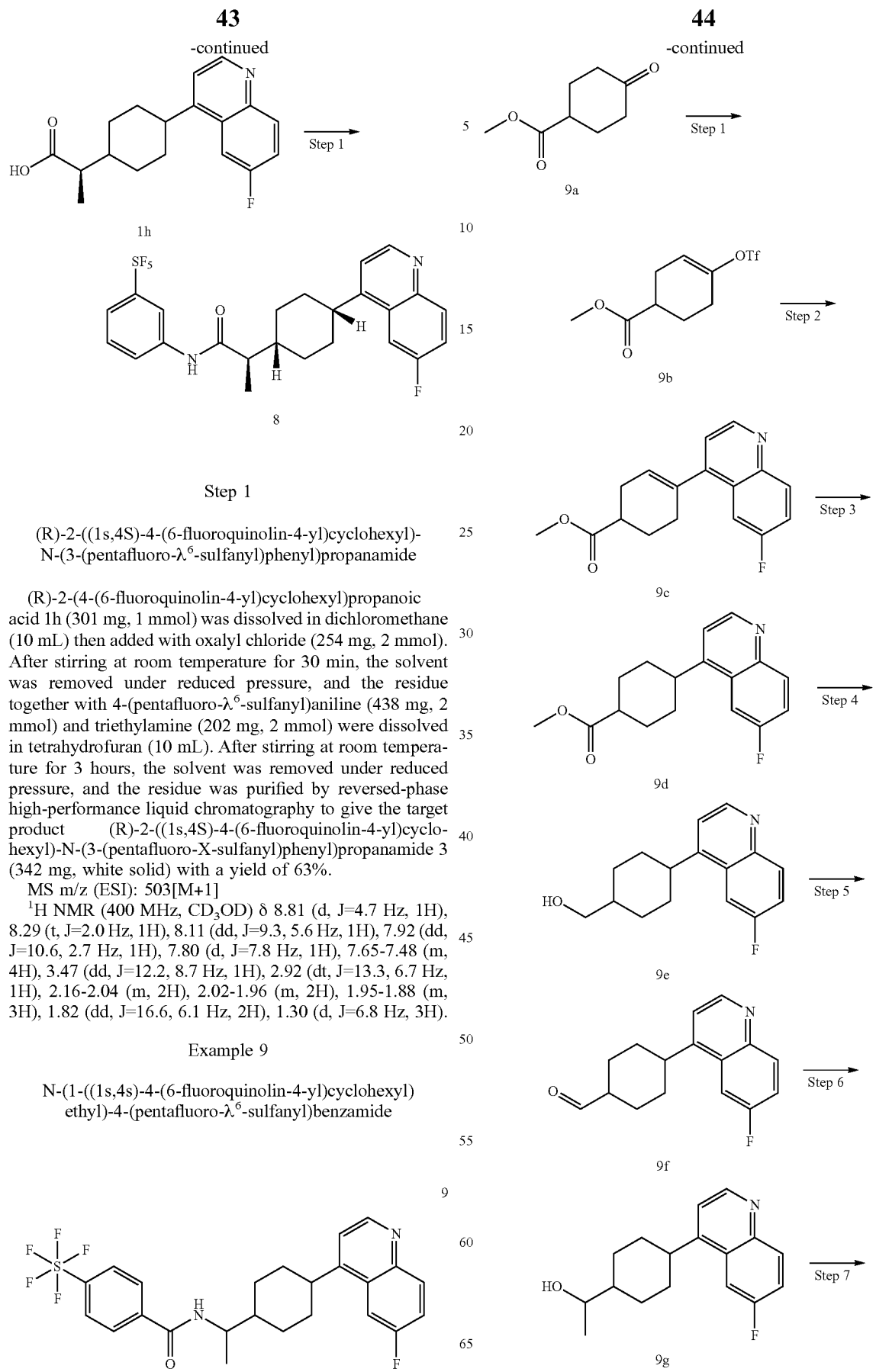

Step 1

(R)-2-((1s,4S)-4-(6-fluoroquinolin-4-yl)cyclohexyl)-N-(3-(pentafluoro-λ⁶-sulfanyl)phenyl)propanamide (R)-2-(4-(6-fluoroquinolin-4-yl)cyclohexyl)propanoic acid 1h (301 mg, 1 mmol) was dissolved in dichloromethane (10 mL) then added with oxalyl chloride (254 mg, 2 mmol). After stirring at room temperature for 30 min, the solvent was removed under reduced pressure, and the residue together with 4-(pentafluoro-λ⁶-sulfanyl)aniline (438 mg, 2 mmol) and triethylamine (202 mg, 2 mmol) were dissolved in tetrahydrofuran (10 mL). After stirring at room temperature for 3 hours, the solvent was removed under reduced pressure, and the residue was purified by reversed-phase high-performance liquid chromatography to give the target product (R)-2-((1s,4S)-4-(6-fluoroquinolin-4-yl)cyclohexyl)-N-(3-(pentafluoro-X-sulfanyl)phenyl)propanamide 3 (342 mg, white solid) with a yield of 63%.

MS m/z (ESI): 503[M+1]

¹H NMR (400 MHz, CD₃OD) δ 8.81 (d, J=4.7 Hz, 1H), 8.29 (t, J=2.0 Hz, 1H), 8.11 (dd, J=9.3, 5.6 Hz, 1H), 7.92 (dd, J=10.6, 2.7 Hz, 1H), 7.80 (d, J=7.8 Hz, 1H), 7.65-7.48 (m, 4H), 3.47 (dd, J=12.2, 8.7 Hz, 1H), 2.92 (dt, J=13.3, 6.7 Hz, 1H), 2.16-2.04 (m, 2H), 2.02-1.96 (m, 2H), 1.95-1.88 (m, 3H), 1.82 (dd, J=16.6, 6.1 Hz, 2H), 1.30 (d, J=6.8 Hz, 3H).

Example 9

N-(1-((1s,4s)-4-(6-fluoroquinolin-4-yl)cyclohexyl)ethyl)-4-(pentafluoro-λ⁶-sulfanyl)benzamide -continued

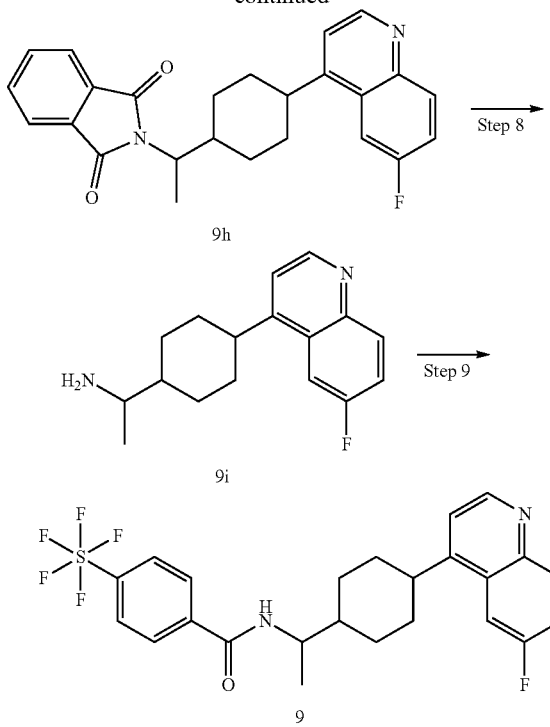

Step 1

Methyl 4-(((trifluoromethyl)sulfonyl)oxyl)cyclohex-3-ene-1-carboxylate 2,6-Di-tert-butyl-4-methylpyridine (4.1 g, 20 mmol) was dissolved in dichloromethane (15 mL), then added with methyl 4-oxocyclohexane-1-carboxylate 9a (1.80 g, 18 mmol) and trifluoromethanesulfonic anhydride (5.7 g, 20 mmol). The reaction mixture was stirred at room temperature for 24 hours under argon atmosphere and filtered. The solvent was removed under reduced pressure, and the residue was washed with ethyl acetate (30 mL×3). The organic phases were combined, washed with cold 1 N hydrochloric acid (50 mL) and saturated brine (50 mL), and then dried over anhydrous sodium carbonate. After filtering, the solvent was removed under reduced pressure to give the target product methyl 4-(((trifluoromethyl)sulfonyl)oxyl)cyclohex-3-ene-1-carboxylate 9b (4.2 g, colorless oil) with a yield of 76%.

$^1$H NMR (400 MHz, CDCl$_3$) δ 5.82-5.68 (m, 1H), 3.70 (s, 3H), 2.60 (ddd, J=10.5, 7.0, 3.3 Hz, 1H), 2.48-2.35 (m, 4H), 2.13 (ddd, J=8.9, 4.1, 1.4 Hz, 1H), 1.93 (ddd, J=6.9, 4.7, 2.6 Hz, 1H).

Step 2

Methyl 4-(6-fluoroquinolin-4-yl)cyclohex-3-ene-1-carboxylate

A mixture of methyl 4-(((trifluoromethyl)sulfonyl)oxyl) cyclohex-3-ene-1-carboxylate 9b (4.2 g, 14.6 mmol), (6-fluoroquinolin-4-yl)boronic acid (2.78 g, 14.6 mmol), 1,1-bis(diphenylphosphino)ferrocene palladium chloride dichloromethane complex (1.19 g, 1.46 mmol), potassium carbonate (403 mg, 2.92 mmol), water (5 mL) and 1,4-dioxane (20 mL) was heated to 100° C. under nitrogen atmosphere and stirred for 2 hours. The reaction mixture was cooled to room temperature and concentrated under reduced pressure. The residue was purified by silica gel column chromatography (petroleum ether/ethyl acetate=20/1 to 1/1) to give the target product methyl 4-(6-fluoroquinolin-4-yl) cyclohex-3-ene-1-carboxylate 9c (3.32 g, light yellow oil) with a yield of 80%.

MS m/z (ESI): 286[M+1]

Step 3

Methyl 4-(6-fluoroquinolin-4-yl)cyclohexane-1-carboxylate

Methyl 4-(6-fluoroquinolin-4-yl)cyclohex-3-ene-1-carboxylate 9c (3.32 g, 11.67 mmol) was dissolved in methanol (50 mL), then added with 10% palladium on carbon (200 mg) and stirred at room temperature for 2 hours under hydrogen atmosphere. After filtration, the filtrate was concentrated under reduced pressure to give the target product methyl 4-(6-fluoroquinolin-4-yl)cyclohexane-1-carboxylate 9d (3.04 g, light yellow solid) with a yield of 91%.

MS m/z (ESI): 288[M+1]

Step 4

(4-(6-Fluoroquinolin-4-yl)cyclohexyl)methanol

The compound methyl 4-(6-fluoroquinolin-4-yl)cyclohexane-1-carboxylate 9d (1.2 g, 4.18 mmol) was dissolved in anhydrous tetrahydrofuran (20 mL), then added with lithium aluminum hydride (190 mg, 5 mmol). After stirring at room temperature for 1 hour, water (0.5 mL), 15% sodium hydroxide solution (1 mL), water (0.5 mL) and anhydrous sodium sulfate (1 g) were added sequentially. After stirring for 15 min, the mixture was filtered and the solvent was removed under reduced pressure to give the target product (4-(6-fluoroquinolin-4-yl)cyclohexyl)methanol 9e (810 mg, light yellow solid) with a yield of 80%.

MS m/z (ESI): 260[M+1]

Step 5

4-(6-Fluoroquinolin-4-yl)cyclohexane-1-carbaldehyde

The compound (4-(6-fluoroquinolin-4-yl)cyclohexyl) methanol 9e (800 mg, 3.08 mmol) was dissolved in dichloromethane (20 mL), cooled to 0° C., then added with Dess-Martin oxidant (1.5 g, 3.7 mmol). After stirring at 0° C. for 2 hours, the mixture was filtered and the solvent was removed under reduced pressure. The residue was purified by silica gel column chromatography (petroleum ether/ethyl acetate=10/1 to 1/1) to give the target product 4-(6-fluoroquinolin-4-yl)cyclohexane-1-carbaldehyde 9f (596 mg, colorless oil) with a yield of 75%.

MS m/z (ESI): 258[M+1]

Step 6

1-(4-(6-Fluoroquinolin-4-yl)cyclohexyl)ethan-1-ol

The compound 4-(6-fluoroquinolin-4-yl)cyclohexane-1-carbaldehyde 9f (1.67 g, 6.47 mmol) was dissolved in anhydrous tetrahydrofuran (20 mL), cooled to 0° C., then added with a solution of methyl magnesium chloride in tetrahydrofuran (3 M, 2.26 mmol, 6.80 mmol) under a nitrogen atmosphere. After stirring for 2 hours, the mixture was quenched with saturated ammonium chloride solution and the solvent was removed under reduced pressure. The residue was purified by silica gel column chromatography (petroleum ether/ethyl acetate=5/1 to 1/1) to give the target product 1-(4-(6-fluoroquinolin-4-yl)cyclohexyl)ethan-1-ol 9g (1.2 g, colorless oil) with a yield of 70%.

MS m/z (ESI): 274[M+1]

Step 7

2-(1-(4-(6-Fluoroquinolin-4-yl)cyclohexyl)ethyl)isoindoline-1,3-dione 1-(4-(6-Fluoroquinolin-4-yl)cyclohexyl)ethan-1-ol 9g (274 mg, 1.93 mmol), phthalimide (162 mg, 1.1 mmol) and triphenylphosphine (314 mg, 1.2 mmol) were mixed, and added with diisopropylazodicarboxylate (243 mg, 1.2 mmol) under nitrogen atmosphere. After stirring at room temperature for 5 hours, the solvent was removed under reduced pressure. The residue was purified by silica gel column chromatography (petroleum ether/ethyl acetate=10/1 to 1/1) to obtain the target product 2-(1-(4-(6-fluoroquinolin-4-yl)cyclohexyl)ethyl)isoindoline-1,3-dione 9h (102 mg, white solid) with a yield of 25%.

MS m/z (ESI): 403[M+1]

Step 8

1-(4-(6-Fluoroquinolin-4-yl)cyclohexyl)ethan-1-amine 2-(1-(4-(6-Fluoroquinolin-4-yl)cyclohexyl)ethyl)isoindoline-1,3-dione 9h (600 mg, 1.5 mmol) was dissolved in ethanol (20 mL) then added with hydrazine hydrate (1 mL). The mixture was heated to 50° C. and stirred for 5 hours. After cooling to room temperature, the solvent was removed under reduced pressure, and the residue was purified by reversed-phase high-performance liquid chromatography to give the target product 1-(4-(6-Fluoroquinolin-4-yl)cyclohexyl)ethan-1-amine 9i (320 mg, white solid) with a yield of 74%.

MS m/z (ESI): 273[M+1]

Step 9

N-(1-((1s,4s)-4-(6-fluoroquinolin-4-yl)cyclohexyl)ethyl)-4-(pentafluoro-$\lambda^6$-sulfanyl)benzamide 1-(4-(6-Fluoroquinolin-4-yl)cyclohexyl)ethan-1-amine 9i (50 mg, 0.184 mmol) and diisopropylethylamine (47 mg, 0.367 mmol) were dissolved in anhydrous tetrahydrofuran (10 mL), then added with 4-(pentafluoro-$\lambda^6$-sulfanyl)benzoyl chloride (49 mg, 0.184 mmol). After stirring at room temperature for 2 hours, the solvent was removed under reduced pressure, and the residue was purified by reversed-phase high performance liquid chromatography to give the target product N-(1-((1s,4s)-4-(6-fluoroquinolin-4-yl)cyclohexyl)ethyl)-4-(pentafluoro-$\lambda^6$-sulfanyl)benzamide 9 (42.1 mg, white solid) with a yield of 42%.

MS m/z (ESI): 503[M+1]
$^1$H NMR (400 MHz, CD$_3$OD) δ 9.12 (d, J=5.7 Hz, 1H), 8.54 (dd, J=34.3, 8.9 Hz, 1H), 8.38-8.27 (m, 2H), 8.14 (d, J=5.8 Hz, 1H), 8.03-8.00 (m, 2H), 7.99-7.95 (m, 2H), 4.71-4.58 (m, 1H), 3.80-3.64 (m, 1H), 2.13-1.86 (m, 9H), 1.35 (d, J=8.0 Hz, 3H).

IDO Cellular Activity Inhibition Assay

The effect of the compounds of the present invention on the activity of indoleamine 2,3-dioxygenase (IDO) in Hela cells induced by IFN-γ was evaluated by the Ehrlich method.

The experimental principle is summarized as follows: IDO expression is low in Hela cells under no induction, but a certain concentration of IFN-γ can induces Hela cells to express IDO which catalyzes the conversion of tryptophan to N-formyl kynurenine, which in turn is hydrolyzed by trichloroacetic acid to give kynurenine. Kynurenine then reacts with the Ehrlich reagent to give a color enabling detection of the IDO activity. The absorbance at 490 nm (OD490) is directly proportional to the IDO activity.

The test compound was dissolved in DMSO (Sigma, Cat. No. D5879) and diluted to 5 mM, then serially diluted 3-fold with DMSO to a minimum concentration of 2.29 µM, and each concentration point was further diluted 50-fold with FBS-free DMEM medium (ThermoFisher, Cat. No. 11995073). If a compound's IC50 value was very low, the initial concentration of the compound was lowered.

Hela cells (ATCC, Cat. No. CCL-2) were cultured in DMEM complete medium containing 10% FBS (GBICO, Cat. No. 10099-141) and 100 U/mL streptomycin mixture (ThermoFisher, Cat. No. 15140122). When covering the culture vessel 80-90%, the cells were digested with 0.25% trypsin (containing EDTA) (ThermoFisher, Cat. No. 25200056) and planted in 96-well plates (Corning, Cat. No. 3599) by 20000 cells per well (80 µL of DMEM medium). The plates were then incubated in a 37° C., 5% CO$_2$ incubator overnight (18-20 hours).

After overnight, 10 µL of DMEM-diluted compound and 10 µL of 500 ng/mL of IFN-γ were added to each well, and gently mixed and the 96-well plates were placed in a 37° C., 5% CO$_2$ incubator for further culturing. After 24 hours, they were removed and centrifuged at room temperature under 2000×g for 5 min, and then the supernatants were transferred to reaction plates (Sigma, Cat. No. CLS3695). One-twentieth of trichloroacetic acid (Sigma, Cat. No. T9159) was added and incubated at 60° C. After 30 min, the reaction plates were centrifuged at room temperature under 2000×g for 5 min. The supernatants were transferred to clean reaction plates, an equal volume of the Ehrlich reagent was added, mixed, and incubated at room temperature. After 15 min, OD490 of each well was measured.

In this experiment, OD490 without IFN-γ but with DMEM medium replacement was referred as OD490$_{100\% \ inhibition}$. OD490 with IFN-γ and 0.2% DMSO was referred as OD490$_{0\% \ inhibition}$. The percentage of inhibition on the IDO1 activity in Hela cells by a compound was calculated using the following formula:

Inhibition %=100−100*($OD490_{compound}$−$OD490_{100\% \ inhibition}$)/($OD490_{0\% \ inhibition}$−$OD490_{100\% \ inhibition}$)

The IC$_{50}$ value of a compound was obtained by fitting 8 concentration points using XLfit software (ID Business Solutions Ltd., UK) following the formula below:

Y=Bottom+(Top−Bottom)/(1+10^((log IC$_{50}$−X)*slope factor))

Where Y is the percentage of inhibition, Bottom is the bottom platform value of the S-curve, Top is the top platform value of the S-curve, X is the logarithm of the concentration of the test compound, and slope factor is the slope coefficient of the curve.

The activity data for part of representative exemplified compounds are listed as follows:

| Compound No. | IC$_{50}$ | Compound No. | IC$_{50}$ |
|---|---|---|---|
| 1 | A | 2 | C |
| 3 | A | 4 | B |
| 5 | A | 6 |   |
| 7 |   | 8 | C |
| 9 | A |   |   |

A < 50 nM;
50 nM ≤ B < 200 nM;
200 nM ≤ C < 1000 nM

The compounds of the present invention have a significant inhibitory effect on IDO activity in cells, preferably with an IC$_{50}$ of less than 200 nM, and more preferably with an IC$_{50}$ of less than 50 nM.

What is claimed is:

1. A compound or pharmaceutically acceptable salt, optical isomer, or mixture thereof, of Formula (IIIa)-(IIIc):

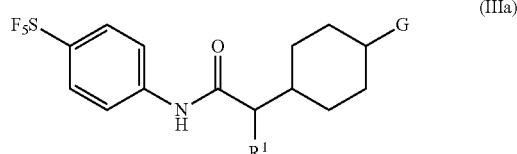
(IIIa)

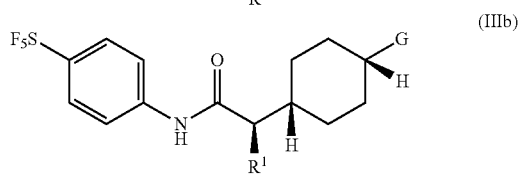
(IIIb)

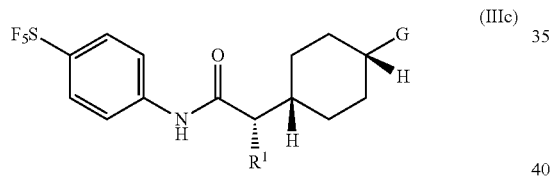
(IIIc)

wherein:
G is a 5-10 membered heteroaryl containing 1-3 nitrogen atoms, optionally substituted with halogen or C$_{1-4}$ alkyl; and
R$^1$ is selected from H and C$_{1-4}$ alkyl.

2. The compound according to claim 1, or pharmaceutically acceptable salt, optical isomer, or mixture thereof, which is a compound of Formula (IV):

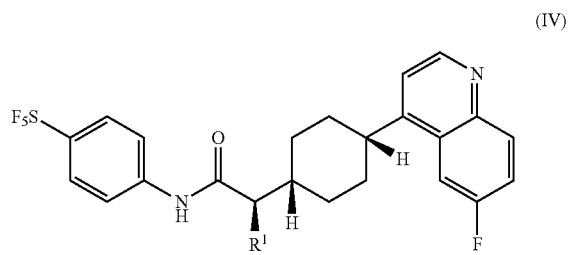
(IV)

wherein:
R$^1$ is C$_{1-4}$ alkyl.

3. The compound according to claim 1 or pharmaceutically acceptable salt, optical isomer, or mixture thereof, which is selected from:

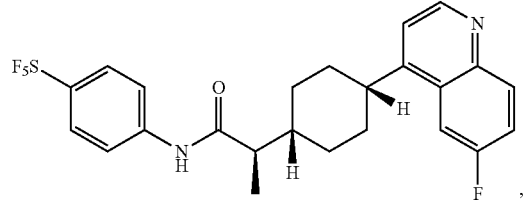,

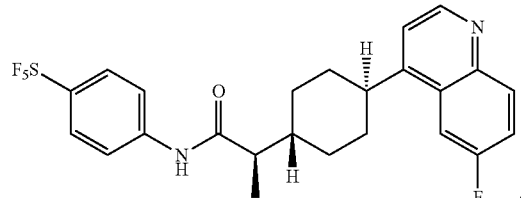,

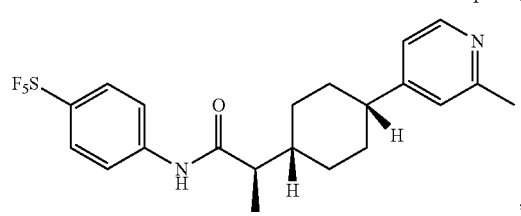,

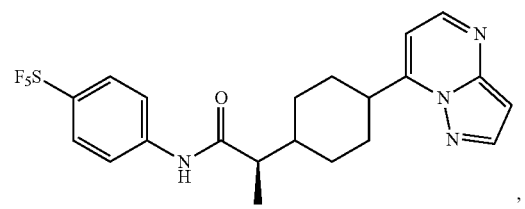,

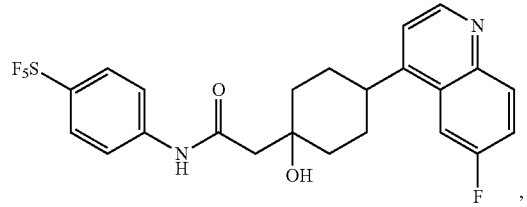,

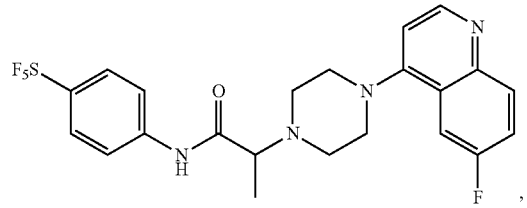,

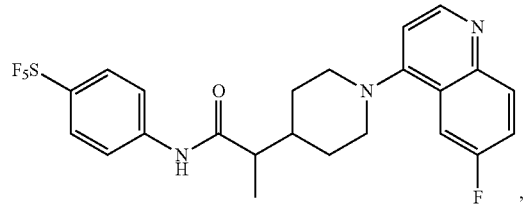,

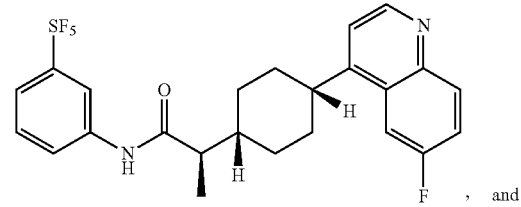, and

-continued

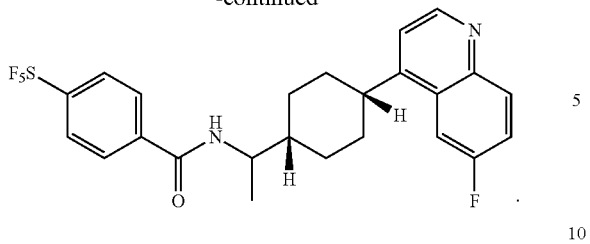

4. A pharmaceutical composition comprising the compound according to claim 1 or pharmaceutically acceptable salt, optical isomer, or mixture thereof, and pharmaceutically acceptable carriers and excipients.

5. The compound of claim 1, or pharmaceutically acceptable salt, optical isomer, or mixture thereof; wherein:

G is selected from quinolyl, pyridyl, and

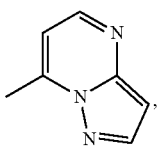

optionally substituted with fluoro or methyl; and $R^1$ is selected from H and methyl.

* * * * *